(12) United States Patent
Agarwal

(10) Patent No.: US 8,417,461 B2
(45) Date of Patent: Apr. 9, 2013

(54) IDENTIFICATION AND MODIFICATION OF DYNAMICAL REGIONS IN PROTEINS FOR ALTERATION OF ENZYME CATALYTIC EFFECT

(75) Inventor: Pratul K. Agarwal, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 463 days.

(21) Appl. No.: 12/244,977

(22) Filed: Oct. 3, 2008

(65) Prior Publication Data

US 2009/0092961 A1 Apr. 9, 2009

Related U.S. Application Data

(60) Provisional application No. 60/997,823, filed on Oct. 5, 2007.

(51) Int. Cl.
*G01N 33/483* (2006.01)
*G01N 33/50* (2006.01)

(52) U.S. Cl. ............................. 702/19; 702/23; 702/27

(58) Field of Classification Search ........................ None
See application file for complete search history.

(56) References Cited

U.S. PATENT DOCUMENTS

2007/0128662 A1 6/2007 Isacoff et al.

OTHER PUBLICATIONS

Mincer et al. J. Phys. Chem. B, 2003, 107 (1), pp. 366-371.*
Agarwal, "Cis/trans Isomerization in HIV-1 Capsid Protein Catalyzed by Cyclophilin A: Insights from Computational and Theoretical Studies", Proteins: Structure, Function, and Bioinformatics 56, 2004, pp. 449-463, Wiley-Liss, Inc.
Agarwal, "Enzymes:An integrated view of structure, dynamics and function", Microbial Cell Factories, Jan. 12, 2006, pp. 1-12.
Agarwal, "Role of Protein Dynamics in Reaction Rate Enhancement by Enzymes", J. Am. Chem. Soc., 2005, pp. 15248-15256, American Chemical Society.
Agarwal, "Network of coupled promoting motions in enzyme catalysis" PNAS, Mar. 5, 2002, pp. 2794-2799, col. 99, No. 5.
Agarwal, Protein Dynamics and Enzymatic Catalysis: Investigating the Peptidyl- Prolyl Cis- Trans Isomerization Activity of Cyclophilin A, Biochemistry, Aug. 24, 2004, pp. 10605-10618, vol. 43, No. 33, American Chemical Society.
Bouvignies et al., "Identification of slow correlated motions in proteins using residual dipolar and hydrogen-bond scalar couplings", PNAS, Sep. 27, 2005, pp. 13885-13890, vol. 102, No. 39.
Bredenbeck et al., "Picosecond conformational transition and equilibration of a cyclic peptide", PNAS, May 27, 2003, pp. 6452-6457, col. 100, No. 11.
Doruker et al., "Dynamics of Large Proteins through Hierarchical Levels of Coarse-Grained Structures", 2001, pp. 119-127, John Wiley & Songs, Inc.
Eisenmesser et al., "Enzyme Dynamics During Catalysis", Science, Feb. 22, 2002, pp. 1520-1523, vol. 295.
Eisenmesser et al., "Intrinsic dynamics of an enzyme underlies catalysis", Nature, Nov. 3, 2005, pp. 117-121, vol. 438, Nature Publishing Group.
Gordon et al., "Interfacing Electronic Structure Theory with Dynamics", J. Phys Chem, 1996, pp. 11512-11525, American Cancer Society.
Haliloglu et al., "Gaussian Dynamics of Folded Proteins", Physical Review Letters , Oct. 20, 1997, pp. 3090-3093, vol. 79, No. 16, The American Physical Society.
Hathorn et al., "Vibrational Normal Modes of Polymer Nanoparticle Dlmers Using the Time-Averaged Normal Coordinate Analysis Method", J. Phys. Chem, 2002, pp. 9174-9180, American Chemical Society.
Leach, "Molecular Modelling", Principles and Applications—Second Edition, pp. 15-16, 273-275, Pearson Prentice Hall, 2001.
Maluendes et al., "A dynamic reaction coordinate approach to ab initio reaction pathways:Application to the 1,5 hexadiene Cope rearrangement", J. Chem. Phys., Oct. 15, 1990, pp. 5902-5911, American Institute of Physics.
Petsko, "Not just your average structures", Nature Structural Biology, Jul. 1996, pp. 565-566, vol. 3, No. 7, Nature Publishing Group.

* cited by examiner

*Primary Examiner* — Michael Borin
(74) *Attorney, Agent, or Firm* — Scully, Scott, Murphy & Presser, P.C.

(57) ABSTRACT

A method for analysis, control, and manipulation for improvement of the chemical reaction rate of a protein-mediated reaction is provided. Enzymes, which typically comprise protein molecules, are very efficient catalysts that enhance chemical reaction rates by many orders of magnitude. Enzymes are widely used for a number of functions in chemical, biochemical, pharmaceutical, and other purposes. The method identifies key protein vibration modes that control the chemical reaction rate of the protein-mediated reaction, providing identification of the factors that enable the enzymes to achieve the high rate of reaction enhancement. By controlling these factors, the function of enzymes may be modulated, i.e., the activity can either be increased for faster enzyme reaction or it can be decreased when a slower enzyme is desired. This method provides an inexpensive and efficient solution by utilizing computer simulations, in combination with available experimental data, to build suitable models and investigate the enzyme activity.

39 Claims, 20 Drawing Sheets

IDENTIFICATION AND MODIFICATION OF DYNAMICAL REGIONS IN PROTEINS FOR ALTERATION OF ENZYME CATALYTIC EFFECT

RELATED APPLICATIONS

This application claims priority to a provisional application titled "Identification and modification of Dynamically Active Protein Residues," filed on Oct. 5, 2007, and having an Application Ser. No. 60/997,823.

STATEMENT REGARDING FEDERALLY SPONSORED RESEARCH OR DEVELOPMENT

This invention was made with United States government support under Prime Contract No. DE-AC05-00OR22725 awarded by the U.S. Department of Energy. The United States government has certain rights in this invention.

FIELD OF THE INVENTION

The present invention relates to the fields of protein biochemistry and molecular biology.

BACKGROUND OF THE INVENTION

Enzymes, a class of proteins, are remarkably well suited for their designated function of accelerating reactions. Naturally occurring enzymes perform this task with great efficiency, enhancing the reaction rates by as many as 17-20 orders of magnitude. Enzymes have been widely used in various laboratory bench work to large scale industrial applications to assist in the increase of desired biochemical and chemical reaction. Enzymes that are efficient or increase the reaction rates by several folds are sought widely for various applications in industry. The rate-enhancement, achieved by enzymes, refers to the ratio of reaction rate that is achieved in presence and in the absence of enzymes.

A number of theories have been proposed for the rate-enhancement achieved by the enzymes. A common aspect shared by these theories is the realization regarding the importance of protein structure—particularly the reaction center or the active-site as shown in FIG. 1. For more than a century, the activity of enzymes has been related to their structure; the "lock-and-key" and "induced-fit" hypotheses have suggested that the structural interactions between enzymes and the substrates play a role in enzyme catalysis. Such a view is incomplete as it fails to explain many aspects of enzyme's biophysical mechanism. In particular, the factors that enable enzymes to provide the large enhancement of reaction rates still remain a mystery.

Recently, an integrated view of protein structure, dynamics, and function is emerging, where proteins are considered as dynamically active machines and internal protein motions are closely linked to function such as enzyme catalysis (Agarwal, "Enzymes: An integrated view of structure, dynamics and function," (2006), Microbial Cell Factories, 5:2). This is considerably different from the paradigm that has prevailed in the past, where proteins were considered more or less rigid entities and only the structural interactions between enzyme and substrate was considered important for enzyme function. A number of recent investigations have provided details about the movement of protein parts and their involvement in enzyme function. Techniques such as X-ray crystallography and small-angle scattering, nuclear magnetic resonance (NMR) studies, hydrogen-deuterium exchange, neutron scattering, biochemical and mutational analysis have provided vital clues at individual time-scales. However, the detailed understanding of protein dynamics requires information over a broad range of time-scales. Moreover, the hydration-shell and bulk solvent fluctuations have been suggested to impact protein dynamics, and therefore, protein function. Theoretical studies and computational modeling have provided novel insights into the link between protein dynamics, solvent fluctuations and enzyme catalysis at multiple time-scales.

Evidence has indicated that internal protein dynamics or the internal motions that occur within proteins promote the protein function such as enzyme catalysis and enables the rate-enhancement achieved by enzymes. Referring to FIG. 2, the protein motions occur over a broad range of time-scales and vary considerably in nature. On one hand, there are fast motions in proteins, occurring at $10^{15}$ times per second. Harmonic bond vibrations are examples of such motions. On the other hand, concerted global motions referred to as breathing motions, spanning large areas of the proteins, occur about $10^6$ times or less per second. Faster motions are relatively localized to atoms and residues; slower concerted motions often involve larger areas, including distant domains. In between, there are a wide variety of motions involving side-chains, concerted motions of atoms within neighboring residues and loop regions, rocking motions of α-helices and concerted motions of β-strands. These collective motions are thus different from random thermodynamic fluctuations. The concerted movement of protein regions described by a set of atomic displacements for atoms in the protein is collectively referred to as a protein vibration mode.

The protein motions observed by experimental studies depend on the ability of the technique to capture these motions at defined time-scales. X-ray crystallography is able to capture the overall deviations of the protein atoms/residues (indicated by large temperature factor) as well as different orientation of loops and α-helix/β-sheets along sub-states of an enzyme reaction (Petsko, "Not just your average structures", (1996), Nat. Struct. Biol. 3: 565-566). NMR studies provide an ensemble of structures showing movement of different protein parts, particularly motion of the flexible loop regions at the nanosecond time-scales or longer (Eisenmesser et al., "Enzyme dynamics during catalysis", (2002), Science 295: 1520-1523; Eisenmesser et al., "Intrinsic dynamics of an enzyme underlies catalysis," (2005), Nature 438: 117-121). Other techniques including neutron and X-ray scattering, hydrogen-deuterium exchange also provide interesting insights at other timescales. Theoretical and computational techniques have been particularly useful in discovering and characterizing a wide range of protein dynamical events, ranging from picosecond to millisecond and longer time-scale (Agarwal et al., "Network of coupled promoting motions in enzyme catalysis," (2002), Proc. Natl. Acad. Sci. USA 99: 2794-2799; Agarwal, "Cis/trans isomerization in HIV-1 capsid protein catalyzed by cyclophilin A: Insights from computational and theoretical studies," (2004), Proteins-Structure Function and Bioinformatics 56: 449-463; Agarwal et al., "Protein dynamics and enzymatic catalysis: investigating the peptidyl-prolyl cis-trans isomerization activity of cyclophilin A," (2004), Biochemistry 43: 10605-10618; Agarwal, "Role of protein dynamics in reaction rate enhancement by enzymes," (2005), J: Am. Chem. Soc. 127: 15248-15256).

Enzyme efficiency is understood in terms of how rapidly an enzyme converts the substrates into products. Enzyme rate kinetics describes the modeling of enzyme activity in terms of various factors that influence the conversion of substrate into products. Transition state theory (TST) framework is commonly used for modeling enzyme reactions. In this framework a chemical reaction in the condensed phase (such as enzyme catalysis) may be described in terms of a free energy profile (see FIG. 3).

The free energy profile is generated as a function of a reaction coordinate, which describes the progression of the enzyme reaction. The reaction coordinate can be a single geometrical quantity (internal degree of freedom of the protein) or it could be a collection of various geometrical changes including the protein and the solvent (collective reaction coordinate). The overall rate ($k_{obs}$) may be expressed as the product of an equilibrium transition state theory rate ($k_{TST}$), which is directly related to the activation free energy barrier ($\Delta G$), and the transmission coefficient ($\kappa$), which accounts for the dynamical re-crossings of the barrier, i.e., $$k_{obs} = \kappa k_{TST} \text{ and } k_{TST} = \left(\frac{k_B T}{h}\right) e^{-\Delta G/k_B T}.$$

Within this framework, the internal protein dynamics can influence the enzyme catalysis in two distinct ways. First, enzymes are dynamical systems, which have an impact on reaction rates by altering the active-site environment such that more trajectories become productive after successful barrier crossing. FIG. 3 illustrates the behavior of two reaction trajectories close to the transition state (TS). The first trajectory returns to the reactant side (non-productive), while the second trajectory crosses the barrier several times before reaching the product state (productive). Transmission coefficient ($\kappa$) is a pre-factor which corrects the TST reaction rate for the number of barrier re-crossings. Secondly, the activation energy barrier ($\Delta G$) can also be decreased by the internal protein dynamics, therefore, impacting the enzyme rate kinetics. Transmission coefficient and activation energy barrier are expected to be different for reaction in the presence and absence of the enzyme. This gives rise to the rate-enhancement achieved by the enzyme.

Recent developments have revealed how the internal protein dynamics is connected to the enzyme mechanism of conversion of substrates to product as well as the rate-enhancement property of enzymes (Agarwal et al, 2004, *Biochemistry* 43: 10605-10618; Agarwal, 2005, *J: Am. Chem. Soc.* 127: 15248-15256). Methods have been developed to identify and characterize the slow conformational fluctuations that occur in the enzymes at the time-scale of the reaction. Currently, single computer simulations using molecular dynamics techniques can only model a few nanoseconds ($10^{-9}$ s); however, the common enzyme reactions occur on microsecond-millisecond ($10^{-6}$-$10^{-3}$ s) time-scales. FIG. 4 depicts the use of umbrella sampling technique to sample protein conformations along the various sections of the reaction coordinate using simultaneous molecular dynamics runs. A number of molecular dynamics runs covering the entire reaction pathway are used with biasing potential that allows sampling of higher energy regions. The entire of protein conformations collected can be analyzed by method such as quasi-harmonic analysis (QHA) or related methods to identify the slow conformational fluctuations or the protein vibrational modes corresponding to the microsecond-millisecond time-scales. Further characterization can identify the protein vibrational modes that are closely linked (or coupled) to the enzyme reaction under investigation.

Recent developments have identified the role of protein motions in connection with the rate-enhancement of enzymes. The important protein vibrational modes and the associated enzyme residues form a network of protein vibrations/motions promoting catalysis as depicted in FIG. 5. The role of these dynamical movements and network residues is to provide the thermo-dynamical energy to conduct the reaction. Energy is required to overcome the reaction activation energy barrier, in some enzyme systems this energy is supplied by a chemical source that is coupled to the enzyme reaction such as the hydrolysis of small molecule. However the majority of enzymes (particularly the ones with industrial applications) work without any source of chemical energy to overcome the energy barrier. Energy associated with thermodynamic fluctuations of the solvent surrounding the protein is expected to provide the energy to the active-site. Therefore, thermodynamical coupling between the solvent and the internal protein dynamics plays an important role in enzyme efficiency and rate kinetics. Enzyme shape and its organization of protein residues are closely connected to the transfer of energy from the solvent (regions on the surface of the enzyme molecule) to the active-site (internal region where the biochemical reaction takes place) as shown in FIG. 5.

FIG. 6 exemplifies instances of this network, which extends from surface regions to active site, and is a conserved part of enzyme structure and has a role in promoting catalysis. In FIG. 6 depicts, a network of protein vibrations in enzyme cyclophilin A, coupled to its catalytic activity of peptidyl-prolyl cis-trans isomerization (PPIase) that has been recently discovered. Theoretical investigations of concerted conformational fluctuations occurring on microsecond and longer time scales within the discovered network indicated that protein dynamics promotes catalysis by altering transition state barrier crossing behavior of reaction trajectories. An increase in transmission coefficient and number of productive trajectories with increasing amounts of kinetic energy in vibration modes has been observed. Variations in active site enzyme-substrate interactions near transition state are found to be correlated with barrier re-crossings. Modeling and simulations also showed that energy transferred from first solvation shell to surface residues impacts catalysis through network fluctuations. The detailed characterization of network has indicated that protein dynamics plays a role in rate enhancement by enzymes. Similarly the impact of protein dynamics on reaction barrier has been observed. The impact of making enzyme rigid indicates that the activation energy barrier increases, indicating that the dynamically active enzymes are suitable for promoting catalysis and enabling rate-enhancement.

The identified network plays a role in enzyme reaction rate-enhancement by increasing the transmission coefficient. FIG. 7 illustrates a new approach for investigating the effect of protein vibrations on reaction trajectories by adding kinetic energy (KE) to specific parts of the enzyme-substrate complex or the hydration-shell solvent. This approach may be considered analogous to the dynamics reaction path (DRP) method previously used to investigate small chemical systems (Gordon et al., "Interfacing electronic structure theory with dynamics," (1996), *J. Phys. Chem.* 100: 11 5 12-1525). In the DRP method, KE is added to one or more of the vibration modes of the system. Originally developed for semi-empirical wavefunctions and subsequently extended by Maluendes and Dupuis, "A dynamic reaction coordinate approach to ab initio reaction pathways: Application to the 1,5 hexadiene cope rearrangement," (1990), *J Chem. Physics* 93: 5902-591 1, to ab inito wave functions, DRP was developed to analyze the dynamics of a reaction starting from a TS. In the methods disclosed, KE is added to select protein vibration modes by scaling velocities proportional to atomic displacements indicated in protein vibration mode. The total system energy was kept unchanged by scaling down velocities of the entire system (enzyme, substrate and solvent), according to the following equation:

$$\frac{1}{2}\sum_{i=1}^{N_{enz\text{-}subs}}\sum_{\alpha} m_i[(1-\delta)^{1/2}v_{i\alpha}+\eta\varphi_{i\alpha}]^2 + \frac{1}{2}\sum_{i=1}^{N_{sol}}\sum_{\alpha} m_i(1-\delta)v_{i\alpha}^2 = \frac{1}{2}\sum_{i=1}^{N_{total}}\sum_{\alpha} m_i v_{i\alpha}^2,$$

in which v represents component of velocity for atom i; $m_i$ is the mass of atom; $N_{enz\text{-}subs}$ is the number of solute atoms; $N_{sol}$ is the number of solvent atoms; $N_{total}$ are total atoms in the system; $\alpha$ represents summation over axes x, y, z; parameter $\delta$ represents the amount of energy transferred into the protein vibration mode $\phi$; and $\eta$ is a variable calculated based on the above equation. Scaled velocities ($v''$) for atoms were assigned according to following expressions:

for enzyme-substrate complex $v''_{i\alpha}=(1-\delta)^{1/2}v_{i\alpha}+\eta\phi_{i\alpha}$, and for solvent $v''_{i\alpha}=(1-\delta)^{1/2}v_{i\alpha}$.

Note that system coordinates are not manipulated. In one example, $\phi$ from QHA based on system snapshots from the entire reaction can be used, however, $\phi$ obtained from NMA can also be used. Similar methodology can be used for adding KE to the solvent molecules. Atomic velocities of solvent molecules were scaled to increase KE (total system KE was unchanged). Snapshots with increased KE in the protein vibration mode or the surface solvent molecules are propagated using molecular dynamics and observing the real time dynamical trajectory behavior near the TS.

FIG. 7 shows the change in behavior of trajectories with increasing amount of kinetic energy (KE) present in a reaction coupled vibration mode. The protein vibrational modes were identified using quasi-harmonic analysis (QHA) of enzyme conformational along the entire reaction pathway. In TST framework, the alternation in the behavior of the dynamical trajectory with increased KE in a reaction coupled mode suggests that the protein vibrations influence the reaction by increasing the transmission coefficient ($\kappa$). It has been observed that not all modes promote the reaction, as indicated by analysis of non-promoting modes. Only a very small number of modes show the reaction promoting effect. Further investigations performed by adding varying amounts of energy to see the effect of these vibrations in a short simulation (pico-second time-scale). The trend indicates that smaller amount of kinetic energy present in these modes, which is expected to be present in real system, promotes the reaction at longer time-scales (hundreds of micro-seconds). The biophysical role of the discovered network in the enzyme reaction can be understood by observing changes. Maximum enzyme stabilization occurs close to the TS (consistent with the TS stabilization theory for enzyme catalysis). The role of the reaction promoting vibrations could, therefore, be interpreted as internal protein dynamical events that facilitate in the stabilization of the TS. Overall, these results indicate that the discovered network of protein vibrations has a promoting effect on the enzyme activity, and is therefore, a factor contributing to rate-enhancement.

The role of hydration-shell solvent in enzyme function may be understood by examining the transfer of KE from first hydration-shell to external regions of protein and its effect on the reaction trajectories were investigated. FIG. 8 shows the results from two representative trajectories propagated after increasing the KE of first solvation shell by 5%; within 0.1 picoseconds an increase in KE of external protein regions is observed. These results indicate transfer of energy from solvent to protein residues; with increase in energy of protein residues more than 8 Å away from the surface occurring within a very short time. This transfer of energy into the protein residues impacts the barrier crossing behavior of reaction trajectories. As depicted in FIG. 9, certain trajectories that are otherwise nonproductive cross barrier within a short time-period and become productive trajectories.

Specifically using the outlined methodology, detailed theoretical studies have lead to the discovery of a network of protein vibrations promoting catalysis in Cyclophilin A. This network is formed by chains of conserved residue and hydrogen-bonds starting from the flexible loop regions on the surface and eventually reaching into the active-site (Agarwal et al., "Protein Dynamics and Enzymatic Catalysis: Investigating the Peptidyl-Prolyl cis/trans Isomerization Activity of Cyclophilin A" Biochemistry 43, pp. 10, 605-10,618 (2004)). Detailed biophysical characterization indicates the role of the dynamical events within this network in the rate enhancement achieved by the enzyme (Agarwal, "Role of Protein Dynamics in Reaction Rate Enhancement by Enzymes," J. Am. Chem. Soc. 127, pp. 15, 248-15,256 (2005)). The reaction promoting vibrations transfer energy from the bulk solvent to the active-site allowing trajectories to overcome the activation energy barrier. Moreover, these network vibrations enable strongest interactions between enzyme and substrate near the transition state, which is consistent with the view that enzyme function by stabilization of the transition state. The existence of this network is supported by experimental data and has also been confirmed by NMR relaxation studies (Eisenmesser et al., "Enzyme dynamics during catalysis," Science 295, pp. 1, 520-1,523 (2002); Eisenmesser et al., "Intrinsic dynamics of an enzyme underlies catalysis," Nature 438, pp. 117-121 (2005)). Cyclophilin A is a member of the prolyl-peptidyl isomerases (PPIases) class of enzymes. Detailed structural analyses of PPIases have indicated that residues and interactions that form the crucial points of this network are conserved across several species. The location of the network residues and interactions within the protein scaffold indicates that promoting vibrations are closely related to the overall shape of PPIase fold.

SUMMARY OF THE INVENTION

A method for analysis, control, and manipulation for improvement of the chemical reaction rate of a protein-mediated reaction is provided. Enzymes, which typically comprise protein molecules, are very efficient catalysts that enhance chemical reaction rates by many orders of magnitude. Enzymes are widely used for a number of functions in chemical, biochemical, pharmaceutical, and other purposes. The method identifies key protein vibration modes and dynamical regions that control the chemical reaction rate of the protein-mediated reaction, providing identification of the factors that enable the enzymes to achieve the high rate of reaction. By controlling these factors, the function of enzymes may be modulated, i.e., the activity can either be increased for faster enzyme reaction or it can be decreased when a slower enzyme is desired. This method provides an inexpensive and efficient solution by utilizing computer simulations, in combination with available experimental data, to build suitable models and investigate the enzyme activity.

In one embodiment, methods are provided for increasing the kinetics of a protein-mediated reaction, comprising a)

determining the vibrational mode of an amino acid or a group of amino acids (on the surface) of the protein, and b) contacting the amino acid or amino acids with an activator to increase the energy associated with the amino acid or surface loop region of the protein, wherein the increase in the energy of the amino acid or surface loop increases the kinetics of the protein-mediated reaction, relative to the kinetics of the protein-mediated reaction in the absence of an activator. In some embodiments, the activator may be attached to the protein. The activator may be covalently attached to the protein. The protein may be an enzyme. The protein may be cyclophilin A. The protein may be dinucleotide binding Rossmann fold protein (DBRP).

In another embodiment, methods are provided for enhancing enzymatic activity, comprising: a) identifying a dynamically active residue in the enzyme, and b) reacting the dynamically active residue in the enzyme with an activator to increase the vibration mode of the dynamically active residue, wherein the increase in the vibration mode of the dynamically active residue enhances the activity of the enzyme. In some embodiments, the activator may be attached to the enzyme. For example, the activator may be covalently attached to the enzyme. The vibration mode may be increased in a variety of ways, e.g. mechanically, by high temperature, by light, by optimal pH, by supplementing with a chemical source of energy, or by addition of radioactivity. In the methods, the dynamically active residue may be in the active-site of the enzyme. Alternatively, the dynamically active residue may be outside of the active-site of the enzyme.

In yet another embodiment, modified proteins are also provided, which include: a) one or more identified dynamically active residues, and b) an activator capable of modifying the vibration mode of the one or more identified dynamically active residues. In the modified proteins, the dynamically active residue may be in the active-site of the protein. Alternatively, the dynamically active residue may be outside of the active-site of the protein. The dynamically active residue may be an amino acid. In the modified protein, the activator may be capable of reacting with the dynamically active residue. The activator may be attached to the protein. For example, the activator may be covalently attached to the protein. The modified protein may be an enzyme. The modified protein may be modified cyclophilin A. Alternatively, the modified protein may be dinucleotide binding Rossmann fold protein (DBRP).

In even another embodiment, methods for identification of a candidate compound as a compound that may modify the speed of an enzymatic reaction are provided, which include the steps of: a) providing a modified enzyme comprising an identified dynamically active residue and an activator capable of reacting with the dynamically active residue to increase the vibration mode of the dynamically active residue, b) contacting the modified enzyme with the candidate compound, and c) measuring the speed of the enzymatic reaction, wherein an increase in the speed of the enzymatic reaction, relative to the speed of the enzymatic reaction catalyzed by the modified enzyme but not contacted with the candidate compound, identifies the candidate compound as a compound that may be useful for the modification of the speed of the enzymatic reaction.

In a further embodiment, devices are also provided for modifying the speed of an enzymatic reaction according to the methods described.

In one embodiment, a model for a catalytic reaction mediated by the protein molecule including a description of the reaction pathway may be provided and samples of conformations of the protein molecule along the reaction coordinate may be generated. The plurality of protein vibration modes are selected among protein vibration modes that are prevalent during the catalytic reaction from the samples of conformations of the protein molecule.

Protein regions that show a large conformational fluctuation in the protein molecule in the selected protein vibration mode may be identified. The dynamically active residue is located in the identified protein regions.

A model for the protein-mediated reaction including a description of the reaction coordinate may be provided. Samples of conformations of the protein molecule along the reaction coordinate may be generated from the model. The plurality of protein vibration modes are selected among protein vibration modes that are prevalent during the catalytic reaction from the samples of conformations of the protein molecule.

For example, the protein molecule may be a dinucleotide binding Rossmann fold protein (DBRP) molecule or a cyclophilin A molecule.

The magnitude of atomic displacement of atoms may be increased by at least one of mechanical means, an elevated temperature, light illumination, a change in pH of a solution, supplementary source of chemical energy, and radioactivity.

The increase in the magnitude of atomic displacement of atoms in the selected protein vibration mode enhances the chemical reaction rate of the protein-mediated reaction.

According to another aspect of the present invention, a method of identifying a dynamically active residue that affects a catalytic reaction in a protein molecule is provided. The method includes:

identifying a plurality of protein motions that are prevalent during a catalytic reaction mediated by a protein molecule;

selecting a protein vibration mode from the plurality of protein motions based on a degree of overlap of a reaction coordinate in each of the plurality of protein motions with a reaction coordinate range of the catalytic reaction; and determining a dynamically active regions of the protein (residue or residues) on the protein molecule based in the selected protein motions; and determining the pathway of flow of energy from the surface of the protein to the active-site through a network of enzyme amino acid residues.

According to yet another aspect of the present invention, a method of modifying a chemical reaction rate of a protein-mediated reaction is provided. The method includes:

selecting a protein vibration mode of a protein molecule based on a degree of overlap of a reaction coordinate distribution with a reaction pathway range of a catalytic reaction; or selecting a residue that is coupled to the protein vibration mode of a protein molecule based on a degree of overlap of a reaction coordinate distribution with a reaction pathway range of a catalytic reaction;

determining a dynamically active residue on the protein molecule based on the selected protein vibration mode; and inducing contact between an activator and the dynamically active residue to modify a magnitude of atomic displacement of atoms in the selected protein vibration mode, wherein the modified magnitude alters the chemical reaction rate of the protein-mediated reaction relative to a chemical reaction rate in the absence of the activator.

According to still another aspect of the present invention, a method of identifying a protein molecule with a potential for enhancement of a chemical reaction rate is provided. The method includes:

identifying a plurality of dynamically active residues in each of multiple species of protein molecules based on a set of protein vibration modes, wherein each protein vibration mode in the set is selected based on a degree of overlap of a reaction coordinate distribution with a reaction coordinate range of a catalytic reaction of a protein molecule among the multiple species of protein molecules;

calculating dynamic cross-correlation factors at a time scale of interactions among the plurality of dynamically active residues;

analyzing the interactions among each of the multiple species of protein molecules;

identifying a protein vibration network that conserves the interactions above a level of magnitude among the multiple species of protein molecules; and determining whether the protein vibration network is present in each of the multiple species of protein molecules.

According to even another aspect of the present invention, a modified protein is provided, which includes:

a prototype protein including a dynamically active residue located outside of an active site of the prototype protein; and an activator attached to the dynamically active residue, wherein the activator modifies a magnitude of atomic displacement of atoms in a protein vibration mode, wherein the modified magnitude alters a chemical reaction rate of a reaction mediated by the modified protein relative to a chemical reaction rate mediated by the prototype protein in the absence of the activator.

The dynamically active residue is an amino acid derivative. The protein molecule is an enzyme and the protein-mediated reaction is an enzymatic activity. The activator is attached to the dynamically active residue.

According to further another aspect of the present invention, an apparatus for altering a reaction rate of a protein is provided. The apparatus includes:

an opaque container that holds a solution and including a solvent and a modified protein, wherein said modified protein includes a prototype protein including a dynamically active residue located outside of an active site of the prototype protein and an activator attached to the dynamically active residue, wherein the activator modifies a magnitude of atomic displacement of atoms in a protein vibration mode, wherein the modified magnitude of the atomic displacement alters a chemical reaction rate of a reaction mediated by the modified protein relative to a chemical reaction rate mediated by the prototype protein in the absence of the activator; and a suitable light source contained within said opaque container.

human-biliverdin IX beta-reductase; 6,7-dihydrobiopterin reductase; and pteridine reductase. These enzymes share the common step of catalyzing hydride transfer from cofactor cofactor nicotinamide adenine dinucleotide (NADH) or its phosphorylated form (NADPH).

Figure 18:
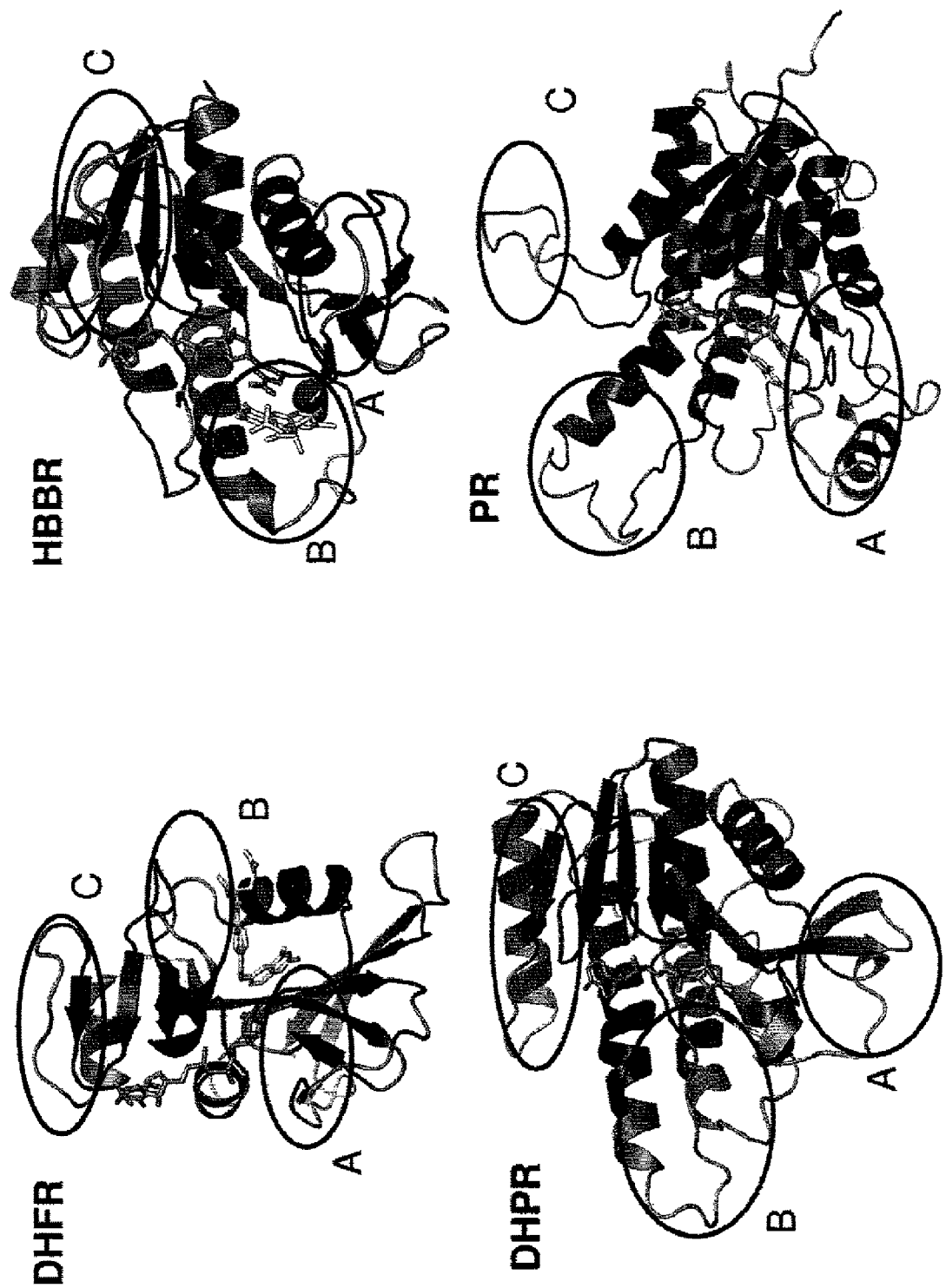

FIG. 18 depicts the surface regions within the DBRP enzyme super-family that are conserved. The results show aggregated flexibility of the top 10 reaction coupled protein vibration modes. The light regions of the protein are most flexible while the dark regions are rigid. The cofactor NAD (P)H is shown as sticks while the substrate is shown as pale color sticks. These regions fall into three clusters A, B and C and show high flexibility. These regions facilitate the collection of energy from the solvent and transfer it into the active-site where it is used for conversion of substrate into product.

Figure 19:
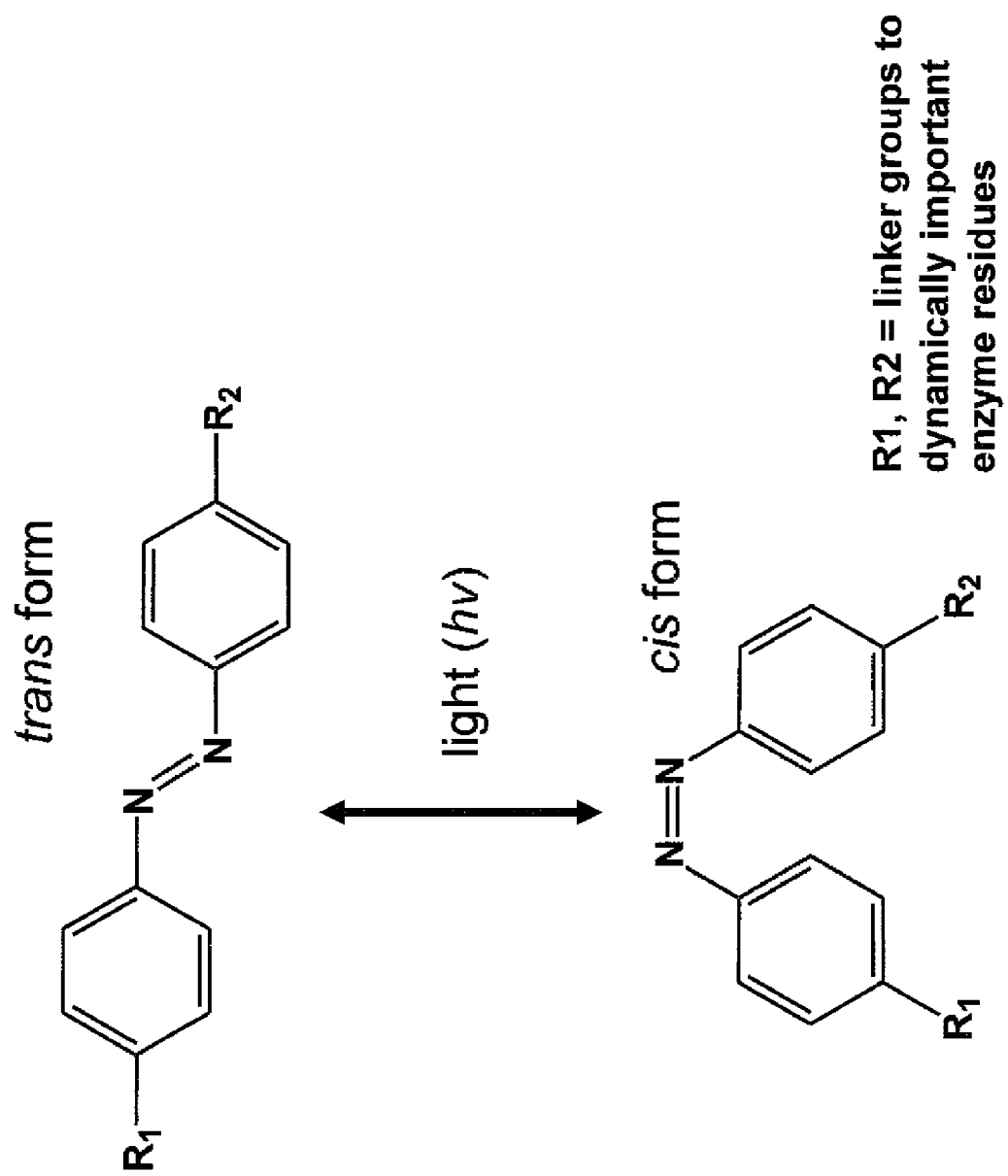

FIG. 19 depicts modification made to the protein with a chemical compound containing the azobenzene group. The azobenzene group is isomerized in presence of light and induces conformational change on the protein surface. This modification provides a way to direct energy from the light source into the enzyme active-site.

Figure 20:
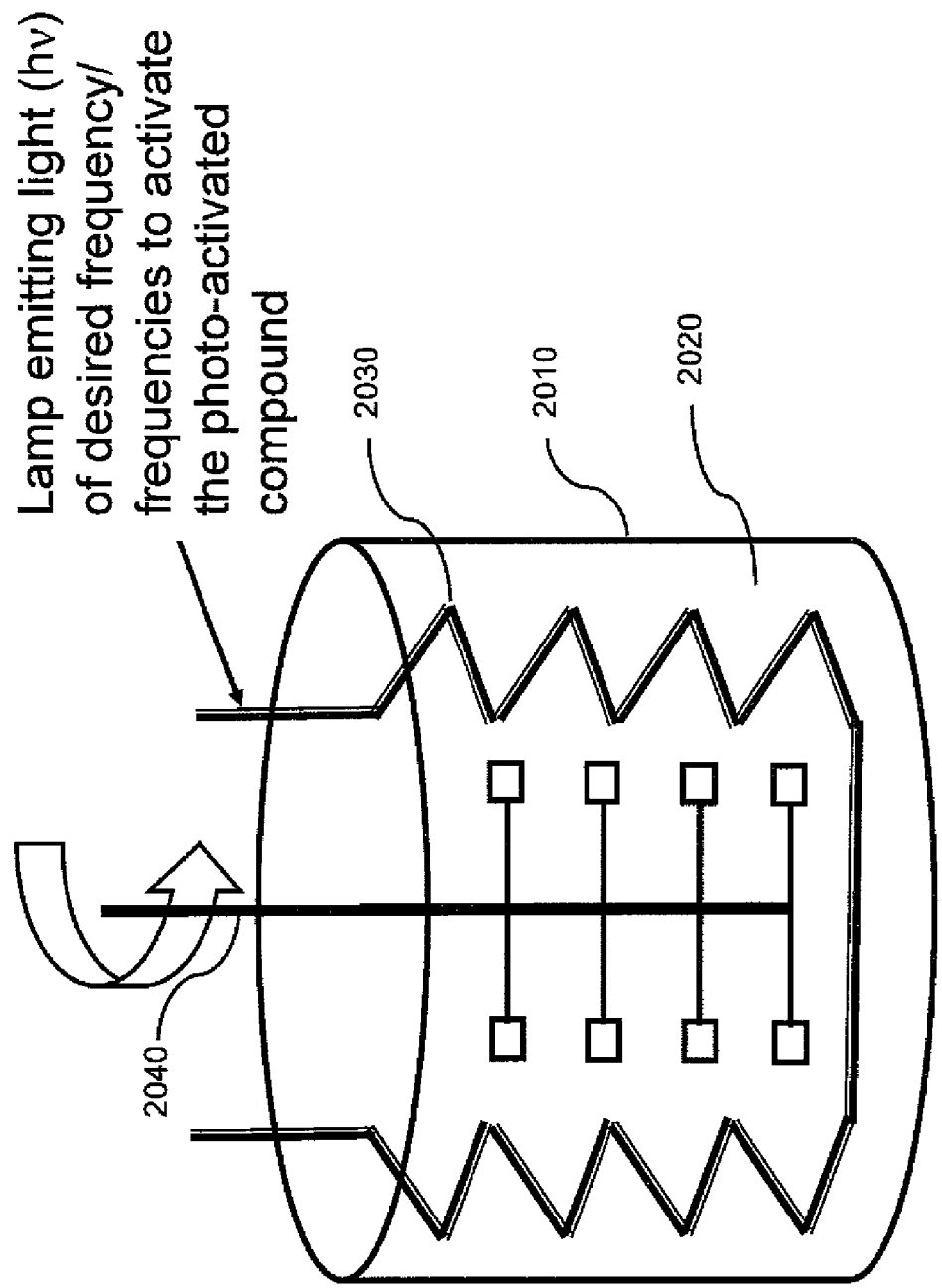

FIG. 20 illustrates one embodiment of a vessel used for practicing the methods of the present invention.

DETAILED DESCRIPTION OF THE INVENTION

As stated above, the present invention relates to protein biochemistry and molecular biology, which are now described in detail with accompanying figures. It is noted that like and corresponding elements mentioned herein and illustrated in the drawings are referred to by like reference numerals. It is noted that proportions of various elements in the accompanying figures are not drawn to scale to enable clear illustration of elements having smaller dimensions relative to other elements having larger dimensions.

Other systems, methods, features, and advantages will be, or will become, apparent to one with skill in the art upon examination of the following figures and detailed description. It is intended that all such additional systems, methods, features and advantages be included within this description, be within the scope of the invention, and be protected by the following claims.

The following terms are employed herein:

As defined herein, "bulk solvent" refers to solvent (typically water) beyond the hydration shell of a protein.

"Hydration shell" refers to the layer of solvent (typically water) closely immediately surrounding a protein.

"Dynamically active protein residues" or "dynamically active residues" refers to one or more protein residues that can change the dynamical properties of a protein. The dynamically active protein residues are typically amino acids. The dynamically active protein residues may be native amino acids. Alternatively, the dynamically active protein residues may be modified amino acids, e.g. myristoilated, phosphorylated, carboxylated, hydroxylated amino acids, etc.

"Cyclophilin A" refers to an enzyme catalyzing the peptidyl-prolyl cis/trans isomerization in proteins and peptides.

"Dinucleotide binding Rossmann fold proteins" (DBRP) refers to a group (super-family) of enzymes that catalyze the transfer of hydride transfer using the cofactor nicotinamide adenine dinucleotide (NADH) or its phosphorylated form (NADPH). The members of this group include the following enzymes: dihydrofolate reductase (DHFR); human-biliverdin IX beta-reductase (HBBR); 6,7-dihydrobiopterin reductase (DHPR); and pteridine reductase (PR).

"Dynamic reaction path" (DRP) refers to a technique for characterizing enzyme (or a small chemical) system after addition of surplus kinetic energy to a specific protein vibration mode or to the molecules of solvent in the hydration shell.

"Normal mode analysis" (NMA) refers to a computational method to compute vibration modes for a single structure.

"Protein dynamics" refers to the internal protein motions that occur in a single molecule on all time-scales, from femtoseconds to seconds and longer. On one side of this range, there are fast and harmonic motions known as vibrations, occurring on femtoseconds to pico-second time-scales. These vibrations involve mainly the movement of bonds, angles, and a few atoms. On the other side, there are collective conformational fluctuations (low-frequency modes) spanning larger areas of protein and occurring on micro-second and longer time-scales. In between these two extremes are motions of individual residues, loop regions and secondary structure elements. These coherent, collective, and repeated movements of many residues spanning different parts of the protein are different from random conformational fluctuations observed in proteins.

"Protein vibrations" and "protein vibrational modes" or "protein vibration modes" refer to the collective coherent conformational fluctuations observed in biomolecules (proteins). These can be computed as a set of atomic displacement vectors and a corresponding period/time-scale for the protein mode. This definition does not lose information about instantaneous fluctuations that that occur in different molecules and does not average out the motions that may occur in different phases of the reaction timescale. Note these are different from random thermal fluctuations.

"PPIase" refers to the peptidyl-prolyl cis/trans isomerization reaction catalyzed by enzymes. The group of enzyme that catalyze this reaction are referred to as PPIases while the structural fold present in these enzymes is referred as PPIase fold.

"Amino acid vibration mode" refers to coherent conformational fluctuations observed in an amino acid (or in amino acid residue). These can be computed as a set of atomic displacement vectors and a corresponding period time-scale for the protein mode. This definition does not lose information about instantaneous fluctuations that that occur in different molecules and does not average out the motions that may occur in different phases of the reaction time-scale. These are different from random thermal fluctuations.

"Quasi-harmonic analysis" (QHA) refers to a technique used to calculate protein vibration mode from a collection of system conformations.

"Rate-enhancement" refers to the ratio of reaction rate in the presence of enzyme and in the absence of enzyme.

"Substrate turnover step" is the step following the binding of substrate to enzyme. In this step, the enzyme converts the substrate from the reactant to the product form.

"X-ray scattering" (XS) and "small angle X-ray scattering" (SAXS) refer to analytical X-ray application techniques for the structural characterization of solid, fluid materials in the nanometer range.

The "active-site" of a protein refers to a protein domain that is structurally, functionally, or both structurally and functionally, active. For example, the active-site of a protein that catalyzes an enzymatic reaction, i.e., an enzyme, refers to a domain that includes amino acid residues involved in binding of a substrate for the purpose of facilitating the enzymatic reaction. As well, the active-site of a protein may refer to a site that includes a protein domain that is involved in protein-protein recognition, protein other molecule recognition, etc. A protein may have one or more active-sites.

"Activator" refers to a compound that may be used to influence the state, energy, or vibration mode of an amino acid residue in a protein. For example, the activator may be used, e.g., to react with an identified amino acid of the protein, to change the energy level, i.e. to activate that amino acid. Examples of suitable activators include photo-activated compounds, caged molecules that can be released upon physico-chemical stimulation, radioactivity-activated compounds, as well as protein molecules that in presence of other small molecules undergo conformational change etc.

The present invention provides methods for identification of protein regions that have a considerable impact on the functioning of the protein including the rate-enhancement achieved by the enzymes. In particular, methods are provided for identification of protein regions outside of the active-site of the protein, which nevertheless have a considerable impact on the functioning of the protein. Areas of a protein that can have direct impact on the activity of the protein are of significant interest as they allow designing of more efficient enzymes through protein engineering. The methods disclosed provide a more efficient way for identifying factors that contribute to the function of the protein and that have an impact on the protein function, through the identification of regions that have impact on protein function and that are located anywhere in the protein, including far away from the active-site and on the surface of the protein.

tion of the molecular dynamics trajectory) is determined according to the time scale of the protein motion to be sampled. For the present invention the sampling intervals that are relevant for providing the protein vibration modes range from $10^{-15}$ seconds to 1 second (either in single trajectory or as a collection of trajectories). In another embodiment the sampling interval is about $10^{-5}$ seconds to about $10^{-6}$ seconds. In another embodiment the sampling interval is about $10^{-15}$ seconds to about $10^{-12}$ seconds. In yet another embodiment the sampling interval is about $10^{-12}$ seconds to about $10^{-6}$ seconds. The sampling interval can be varied from one computer simulation to the next. Longer sampling intervals allow computations of the slower vibration modes, which have implications in overcoming larger energy barriers. In addition to single molecular dynamics trajectories to identify vibration modes at the time-scale of the enzyme reaction, additional computational techniques such as umbrella sampling can be used. Umbrella sampling is used to sample higher energy conformations with applying restraints with a reference structure that is higher in energy. Table 1 summarizes the time scales of various motions to be sampled and their relevance in identifying protein vibration modes with implications in enzyme rate-kinetics.

TABLE 1

Summary of motions in proteins

| | Fast | Intermediate | Slow |
|---|---|---|---|
| Time-scale(s) | $10^{-15}$ to $10^{-12}$ s | $10^{-12}$-$10^{-6}$ s | >$10^{-6}$ s |
| Regions of proteins involved | Few atoms, single residue or side-chain atoms | Few amino acid residues, loop regions, alpha-helices and beta-sheets | Larger regions of proteins and even entire protein; single or multiple domains |

Figure 10:
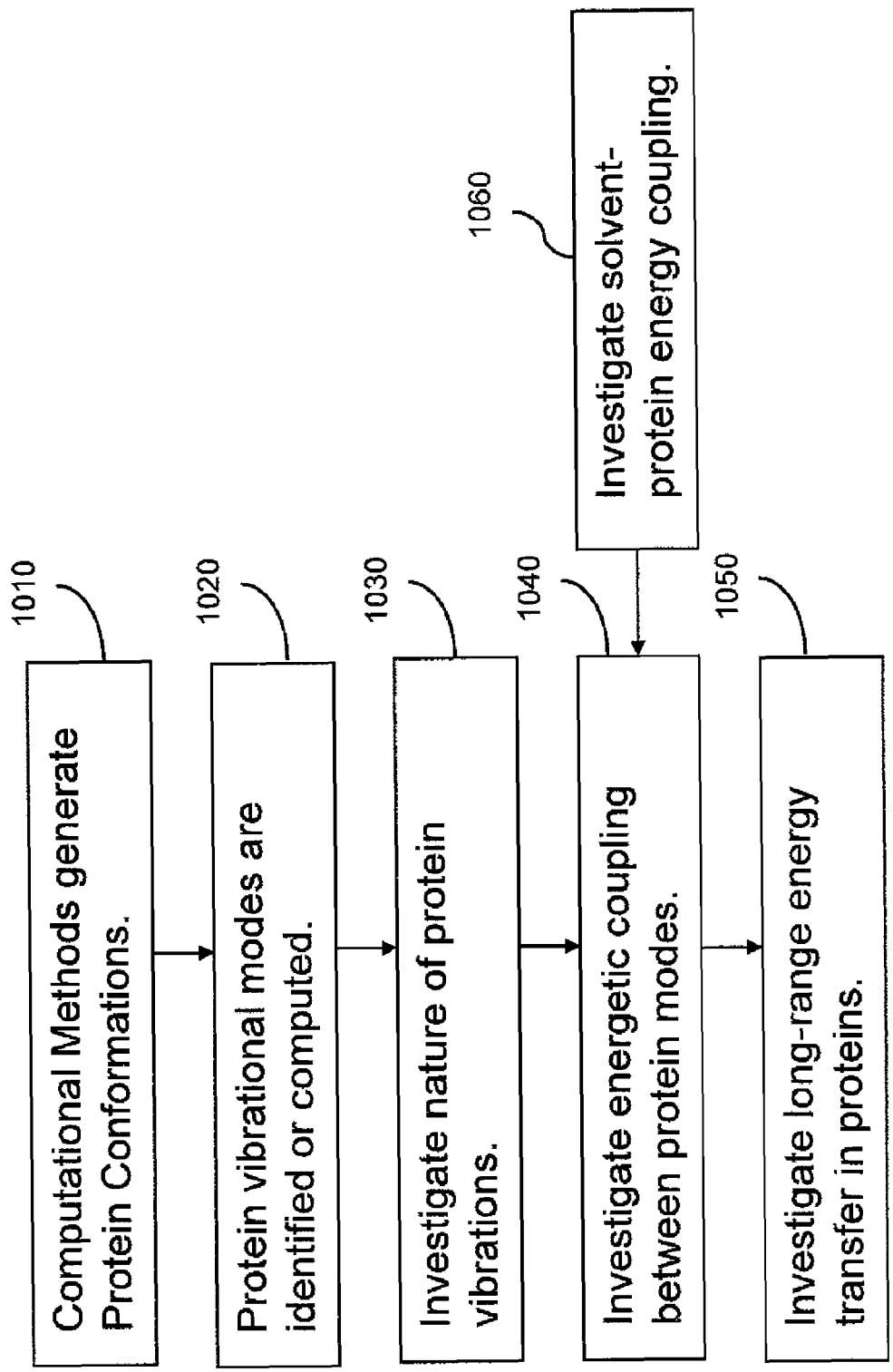
FIG. 10 is a flow diagram illustrating exemplary methodology for investigating the nature of protein vibrations.

The compositions and methods disclosed are in part based on a deeper understanding of the interplay between enzyme structure, dynamics and function, which is reviewed in Agarwal, 2006, *Microbial Cell Factories* 5: 2; Agarwal, 2005, *J: Am. Chem. Soc.* 127: 15248-15256. The dynamical motions that span over entire proteins can have direct influence on the protein function through transmission of energy over short and long distances. This capability of the enzymes facilitates the flow of energy from thermo-dynamical fluctuations of the solvent surrounding the protein to the active-site. Some of these dynamical events and the related structures are conserved parts of many proteins. Small modifications in these conserved structures, even if far away from the reactive center, can have large changes in the protein function due to altered dynamical properties of the protein Referring to FIG. 10, a flow chart illustrates a non-limiting exemplary method of the present invention for investigating long-range energy transfer in proteins associated with protein dynamics.

Referring to step 1010, computational methods are employed to generate protein conformations. Any method known in the art may be employed to generate a list of protein conformations for any given protein molecule.

Referring to step 1020, dynamically active regions in the proteins are identified. This may be effected, by identification of the protein motions at various time-scales first, followed by quantification of the impact of the motions on the enzyme rate-kinetics. In one embodiment the protein motions are identified by using computational methods such as molecular dynamics trajectories. The sampling interval (that is the dura- Computation of the Protein Vibration Modes Vibrational modes of a protein are modeled by a set of displacement vectors for each atom in the protein. Several methods are available to compute the vibration modes of a molecular system such as a protein. A list of suitable methods for use with this invention to compute the protein vibration modes are discussed below:

Normal Mode Analysis (NMA):

This method computes vibration modes of a molecular system by diagonalization of the Hessian matrix (see Molecular Modeling: Principles and Applications, A. R. Leach, Pearson Education Limited/Prentice Hall (Essex, England), 2nd Edition (2001) pages: 273-275). Assuming the molecular system has N atoms, the Hessian matrix is a 3N×3N matrix. The elements of the matrix are the second order energy derivatives with respect to the displacement of atomic positions in the x, y, z directions. The elements can be computed analytically or computationally. Once the Hessian matrix is computed, it is diagonalized to solve for the eigenvectors and eigenvalues of the equation, $\epsilon_i F = \epsilon_i \omega_i$.

The time-scale of molecular vibration is determined by taking the inverse square root of the eigenvalues ($\epsilon$) obtained after diagonalization (Molecular Modeling: Principles and Applications, A. R. Leach, Pearson Education Limited/Prentice Hall (Essex, England), $2^{nd}$ Edition (2001) pages: 15-16). The eigenvector ($\omega$) corresponding to the eigenvalue represents the vibration modes, which are a set of displacement vectors for the atoms in the molecular or the protein conformation.

Time-Averaged Normal Coordinate Analysis (TANCA):

This method is similar to NMA in the sense that the protein vibration modes are obtained by diagonalization of the Hessian matrix (Hathom B. C. et al., "*Vibrational Normal Modes of Polymer Nanoparticle Dimers Using the Time-Averaged Normal Coordinate Analysis Method*," (2002), *J. Chem. Phys. A.*, 106 (40): 9174-9180). However, NMA suffers from some limitation when considering a highly flexible molecular system such as a protein. NMA uses a reference structure and the eigenvalues and eigenvectors thus obtained are only relevant to the reference starting structure. The method therefore weights highly toward the high frequency motions and less toward the low frequency motions. Moreover the low frequency obtained using NMA are not reliable for molecular conformations that differ considerably from the reference structure for NMA.

Techniques such as TANCA can partially overcome this problem by diagonalization of the Hessian matrix which has been constructed numerically by averaging the elements over time. This allows the fast frequency motions to be removed by averaging and provides more accurate low frequency modes that are relevant for enzyme function. More details about this method are available in the references mentioned in the last paragraph.

Quasi-Harmonic Analysis (QHA):

This method computes protein vibration modes from a set of protein conformations that are sampled using either the molecular dynamics (or Monte-Carlo) type simulations. QHA is a powerful method in obtaining vibration modes that are representative of longer time-scales or the low frequency vibration, by utilizing the information from a set of structures which may be separated by a long time scale—or from different parts of the protein conformational space. The vibration modes are obtained by diagonalization of the atomic fluctuation matrix. For a protein with N atoms, the atomic fluctuation matrix, F is a symmetric 3N×3N matrix with term $F_{\alpha\beta}$ defined as:

$$F_{\alpha\beta} = \langle m_\alpha^{1/2}(x_\alpha - \langle x_\alpha \rangle)m_\beta^{1/2}(x_\beta - \langle x_\beta \rangle)\rangle$$

where $\alpha, \beta$ run through the 3N degrees of freedom in Cartesian space and $m_\alpha$ is the mass of atom corresponding to the αth degree of freedom and $x_\alpha$ are the Cartesian coordinates of the atom corresponding to the αth degree of freedom. Quantities in < > denote an average determined from molecular dynamics simulation. To obtain the eigenmodes (vibrational modes) diagonalization of the atomic fluctuation matrix is performed. The time-scale of protein vibration is determined by taking the inverse square root of the eigenvalues ($\epsilon$) obtained after diagonalization (Molecular Modeling: Principles and Applications, Author A. R. Leach, Pearson Education Limited/Prentice Hall (Essex, England), 2$^{nd}$ Edition (2001) pages: 15-16). The eigenvector ($\omega$) corresponding to the eigenvalue represents the protein vibration modes, which are a set of displacement vectors for the atoms in the protein confirmation. Note one of the benefits of QHA is that multiple molecular dynamics trajectories can be combined to construct the atomic fluctuation matrix—thus allowing vibration modes to be computed that represent conformational changes between different areas of the protein conformational space.

Gaussian Network Model (GNM)

This type of calculation uses coarse-grained normal mode analysis to obtain protein vibration modes (Doruker P, et al., (2002) J. Comput. Chem. 23 (1):119-127 and Haliloglu T, et al., (1997). Phys. Rev. Lett. 79 (16):3090-3093). These calculations use a simple parameter harmonic potential for the particles in the system. The eigenmodes are obtained by the diagonalization of Kirchhoff's matrix, which is similar to Hessian matrix, but uses a reduced model of the protein and treats the protein motions as Gaussian type motions.

Irrespective of the type of method described above, for a protein with N atoms, there are 3N–6 protein vibration modes. These modes describe a variety of motions within the protein (see Table 1). The modes with fast time-scales indicate repeated movements of atoms, or a small group of atoms that occur as many as a billion to trillion times per second. The intermediate time scales are associated with concerted movements of a group of protein residues. The intermediate time-scales span several orders of magnitude and are associated with motions of loop regions, alpha helices and beta-sheets. The modes associated with the slowest time-scales are associated with the overall conformational fluctuations of a protein that involve major domain(s) or even the entire protein. The protein motions at different time-scales correspond to kinetic energy to allow overcoming of a variety of energy barriers encountered by the protein in the folding process. The fastest motions in the range of $10^{-15}$ seconds to $10^{-12}$ seconds, overcome small energy barriers. The intermediate motions in the range of $10^{-12}$ seconds to $10^{-6}$ seconds are important for overcoming medium height barriers. The slowest motions at scale of $10^{-6}$ seconds and slower (i.e. >$10^{-6}$ seconds) are important for overcoming large energy barriers. Therefore using vibration modes associated with the slowest motions can find conformations within the conformational energy landscape that are separated by high energy barriers. Likewise the vibration modes associated with the intermediate and faster motions are useful for inducing more local conformational changes, like the movement of a loop region, an alpha helix, or the side chains of individual residues. Accurate estimates of energy associated with the protein vibration modes is currently not available, however, the lower estimations would correspond to energy associated with vibrations of individual bonds (<1 kcal/mol) and on the higher end correspond to movement of entire protein domains (5-10 kcal/mol or higher).

Referring to step 1030, the nature of protein vibrational is characterized either by inspecting the protein vibrational modes that are obtained using methods such as QHA or NMA and related methods. Further experimental methods such as NMR, X-ray crystallography, neutron scattering or hydrogen/deuterium exchange methods could be used to obtained detailed informational about these modes. Of particular interest are the protein regions (one or more amino acid residues) that show large displacements in the vibrational mode. Further interaction of enzyme amino acrid with other active-site amino acid residues or substrate is also deemed important in these vibrational modes.

Figure 12:
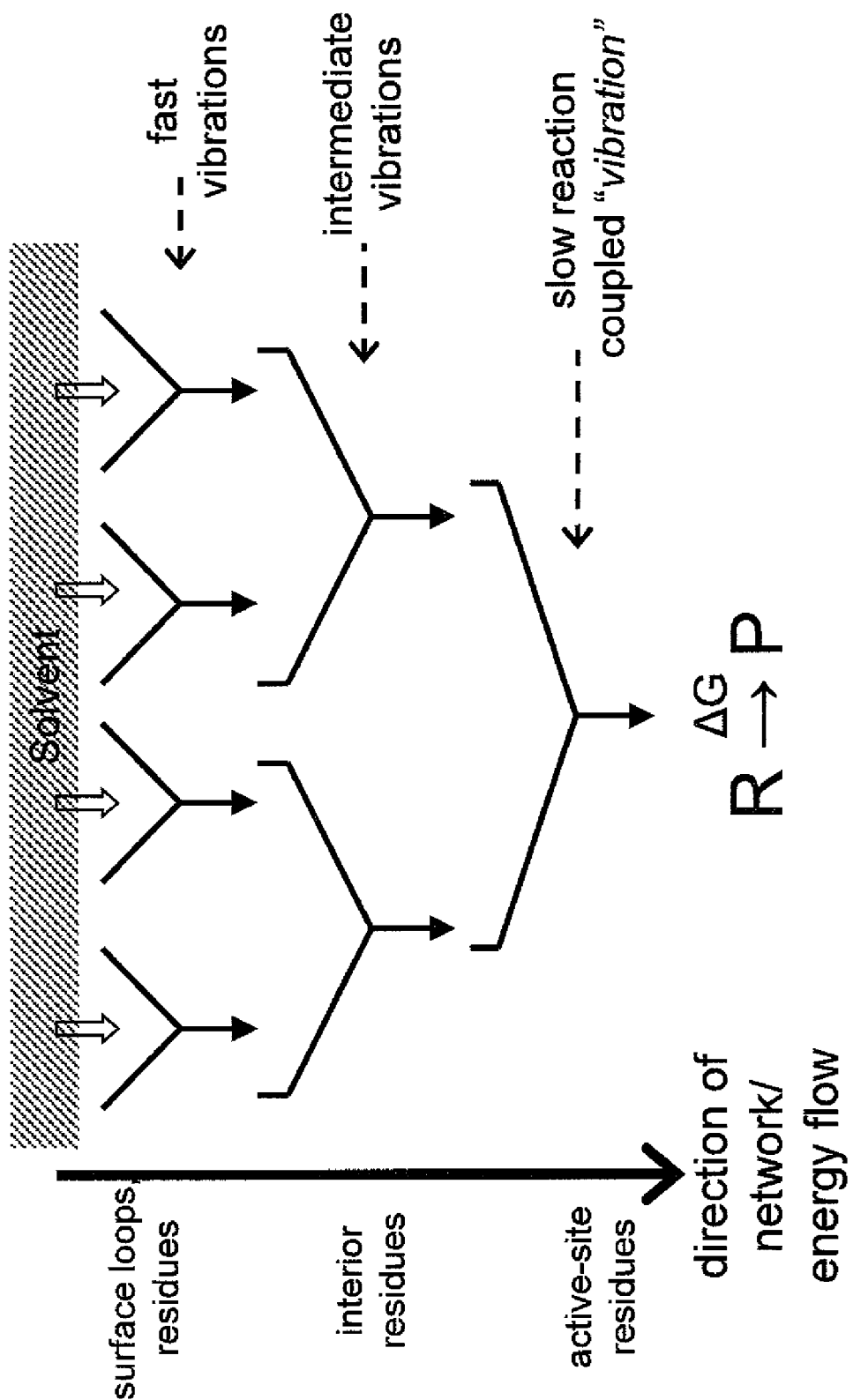
FIG. 12 depicts the energetic flow from the solvent to the active-site through the network pathway and interconnection between various protein vibrations.

Referring to step 1040, solvent-protein energy coupling may be investigated. Optionally, detailed information on the flow of energy from the outside of the protein into the internal regions such as the active-site may be provided employing step 1060. FIG. 12 illustrates the coupling of dynamical motions of solvent with protein residues on surface can lead to transfer of energy, moreover the coupling of fast, intermediate and slow protein conformational fluctuations eventually leads to energy transfer from the outside of the enzyme into the active-site.

Referring to step 1050, the analysis of protein vibrations and the protein amino acid residues involved in the long range energy transfer from the surface of the protein to the active-site are characterized for their detailed role.

The identified dynamically active protein residues may be in a protein which is an enzyme. Such dynamically active protein residues can be activated, thereby resulting in modified proteins. For example, the vibration mode of the dynamically active residues can be altered. The activation may include changing the energy of the dynamically active residue, e.g. changing the kinetic energy. In one example, activation may refer to the addition of energy to the dynamically active protein residue. Generally, in such cases the added energy results in increased or enhanced activity of the protein, (e.g. increase in the rate of a biochemical reaction that the protein catalyzes). Activation, (e.g., change of the vibration mode of particular residue(s)), leads to enhanced or increased activity of the modified enzyme.

In one example, the modified protein may have the functionality of catalyzing a chemical reaction having the chemical reaction rate. At least one of an oxygen atom and a hydrogen atom is transferred in the chemical reaction. In this case, the modified protein is in the oxido-reductase family of enzymes.

In another example, the modified protein may have the functionality of catalyzing transfer of at least one functional group in a chemical reaction having the chemical reaction rate. Non-limiting examples of the at least one functional group include an alkyl group, an acyl group, an aldehyde group, an amino group, an acetyl group, a glucosyl group, and a phosphate group. In this case, the modified protein is in the transferase family of enzymes.

In even another example, the modified protein may have the functionality of catalyzing a chemical reaction having the chemical reaction rate. A water molecule is transferred in the chemical reaction. In this case, the modified protein is in the hydrolase family of enzymes.

In yet another example, the modified protein has the functionality of catalyzing a chemical reaction having the chemical reaction rate. At least one group of atoms is removed without hydrolysis in the chemical reaction. In this case, the modified protein is in the lyase family of enzymes.

In still another example, the modified protein has the functionality of catalyzing a chemical reaction having the chemical reaction rate. At least one atom is rearranged within a molecule in the chemical reaction. In this case, the modified protein is in the isomerase family of enzymes.

In a further another example, the modified protein has the functionality of catalyzing a chemical reaction having the chemical reaction rate. Two molecule are joined in the chemical reaction. In this case, the modified protein is in the ligase family of enzymes.

Figure 11:
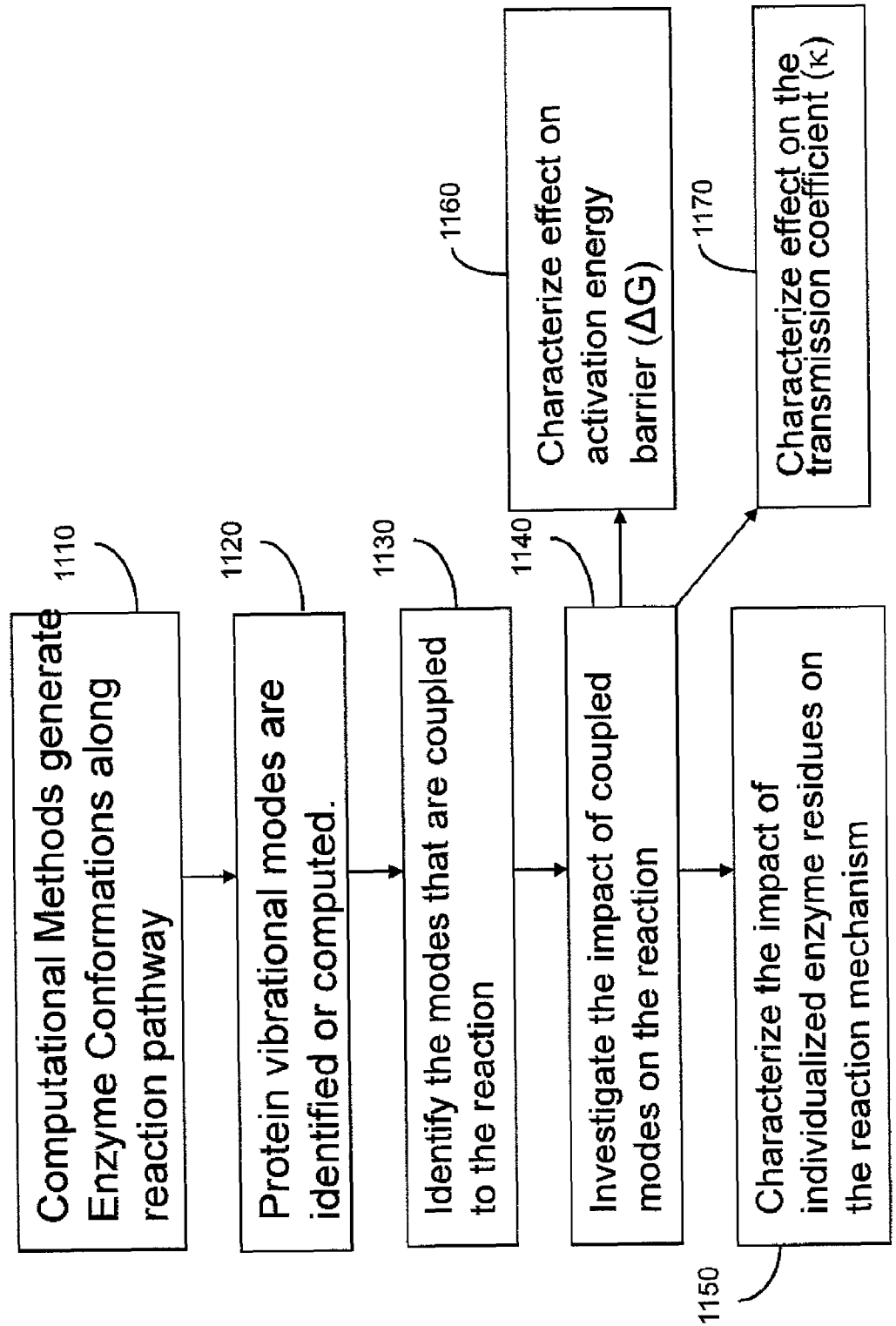
FIG. 11 is a flow diagram illustrating exemplary methodology for investigating the role of protein dynamics in enzyme catalysis.

Referring to FIG. 11, a flow chart illustrates a non-limiting exemplary method of the present invention. According to this method, the identification of the network of protein vibrations and the energy flow in a protein are effected using the following steps:

Referring to step 1110, the enzyme reaction is modeled using a suitable description of the reaction coordinate (Rxn). This can be performed computationally by taking the crystal or NMR structure and using technique such as molecular dynamics and umbrella sampling or some other related technique. The enzyme-substrate conformations are sampled along the reaction coordinate during these simulations.

The protein motions in the enzyme molecule may be computed by identifying protein vibration modes coupled with the catalytic reaction. For example, quasi-harmonic analysis of conformations of the enzyme molecule along a reaction pathway may be employed.

Referring to step 1120, the conformations sampled along the reaction coordinate are used to compute protein vibration mode that are prevalent at the time-scale of the enzyme reaction. Methods such as quasi-harmonic analysis or normal mode analysis are other suitable methods as described above for computation of such protein vibration modes.

The atomic displacement component of each atom in the one of the plurality of protein vibration modes is calculated employing at least one of normal mode analysis on the protein molecule, principal component analysis on the protein molecule, experimental analysis based on nuclear magnetic resonance (NMR) on the protein molecule, experimental analysis based on X-ray crystallography, and experimental analysis based on neutron scattering on the protein molecule.

In one example, the atomic displacement component of each atom in the one of the plurality of protein vibration modes may be calculated by performing Quasi-Harmonic Analysis (QHA) calculation on the protein molecule.

Referring to step 1130, from the set of computed vibration modes, select the computed vibration modes that are coupled to the reaction are selected from the set of prevalent computed vibration modes that are identified at step 1120. This selection is based on finding the modes with largest overlap with the reaction coordinate (Rxn). For example, if the reaction is cis-trans isomerization of peptide bond, the modes that show largest deviation in the peptide-bond angle (reaction coordinate) are considered as coupled to reaction coordinate.

Further, a plurality of protein vibration modes that are prevalent during the protein-mediated reaction may be identified, and the protein vibration mode from the plurality of protein vibration modes may be selected based on the degree of overlap of the reaction coordinate distribution in each of the plurality of protein vibration modes with a reaction coordinate range of the protein-mediated reaction.

The protein vibration mode is selected from a plurality of protein vibration modes. In this case, a first overlap is defined as the overlap between a reaction coordinate distribution of each of the plurality of protein vibration modes with a reaction coordinate range of a catalytic reaction, which is mediated by the prototype protein, per unit (of suitable geometrical quantity used to describe the reaction coordinate) increase in a protein vibration mode. A second overlap is defined as an overlap between any of the rest of all protein vibration modes of the prototype protein that exclude the plurality of protein vibration modes with the reaction coordinate range of the catalytic reaction. The first overlap is greater than any second overlap. The number of protein vibration modes in the plurality of protein vibration modes is a reasonably small number that does not overburden a computational system. For example, the number may be 100, 30, 10, or 3. In one case, the plurality of protein vibration modes may be narrowed down to a single protein vibration mode.

Another protein vibration mode from the plurality of protein vibration modes may be selected based on the degree of overlap of reaction coordinate distribution in each of the plurality of protein vibration modes with the reaction coordinate range of the catalytic reaction. Conformational fluctuation in the protein molecule in the selected protein vibration mode and the at least another protein vibration mode may then be analyzed. The dynamically active residue is identified by the analyzing of the conformational fluctuation.

The role of enzyme is to overcome the activation energy barrier allowing the reaction to proceed from reactant side to the product side. It has been widely accepted that the enzyme function by lowering the barrier or by decreasing the ΔG. This applies to all enzymes and therefore the described methodology is applicable to all enzymes. The discovered network of protein vibrations is proposed to be the mechanism which the enzyme uses to lower the activation energy barrier by collecting energy from the solvent and relaying it to the active-site. The methods therefore use these energy flow pathways for selective addition of the kinetic energy allowing to quickly overcoming the barrier.

Referring to step 1140, the reaction coupled modes are analyzed for understanding the detailed conformational fluctuation in the protein structure. The protein regions showing largest fluctuations are identified as members of the network. This information is also checked against the temperature factors that are available from the X-ray structure. Regions with largest fluctuations from reaction coupled vibration modes and X-ray temperature factors are important.

Dynamic cross-correlation factors are calculated at the time-scale of the reaction between different parts of the network residues. These can be used to identify the interactions between network residues.

Another dynamically active residue may be identified and dynamic cross-correlation factors at a time scale of interaction among the dynamically active residue and the at least another dynamically active residue may be calculated.

The dynamically active residue may be identified by determining a degree of overlap of a reaction coordinate distribution of the protein vibration mode with the reaction pathway range of the catalytic reaction.

The network residues and interactions are analyzed further for their conservation along multiple species. The regions which are conserved across evolution are considered to be part of the network of the protein vibrations network.

The method may further include identifying a plurality of protein vibration modes that are prevalent during a protein-mediated reaction in each of the multiple species of protein molecules and selecting the set of protein vibration modes from the plurality of protein vibration modes based on the degree of overlap of the reaction coordinate distribution in each of the plurality of protein vibration modes with the reaction coordinate range of the catalytic reaction.

The method may further include identifying protein regions that show a large conformational fluctuation in each of the multiple species of the protein molecules in the set of protein vibration modes. The dynamically active residue is located in the identified protein regions.

The interactions across a multiple species of protein molecules including the protein molecule may be analyzed and a protein vibration network of interactions may be identified. The protein vibration network of interactions is from a surface of the protein molecule to an active site of the protein molecule by which energy is transferred to the catalytic reaction.

The identified network residues and the protein vibration modes are investigated for impact on transmission coefficient as well on the activation energy barrier. This is performed addition of kinetic energy in the vibration modes and looking at the behavior of dynamical trajectories as well making the enzyme rigid and investigating the increase in the energy barrier.

Referring to step 1150, the internal protein dynamics can influence the enzyme catalysis in two distinct ways within the TST framework. The impact of individualized enzyme residues on the reaction mechanism may be characterized. The dynamical behavior of a reaction trajectory along a reaction coordinate of the catalytic reaction may be determined.

The degree of reactivity of the protein molecule is determined based on dynamical behavior of a reaction trajectory along a reaction pathway of the catalytic reaction, wherein the degree of reactivity is computed by identifying a change in transmission coefficient through the reaction pathway by employing a constant system energy model, wherein a total energy of a system remains constant in the constant system energy model, and wherein each velocity component of atoms in the system is scaled down by a constant factor in a computational model for the constant system energy model, and wherein a scalar that is proportional to an atomic displacement component of each atom in one of the plurality of protein vibration modes is added to each velocity component of each atom in the constant system energy model.

Figure 13:
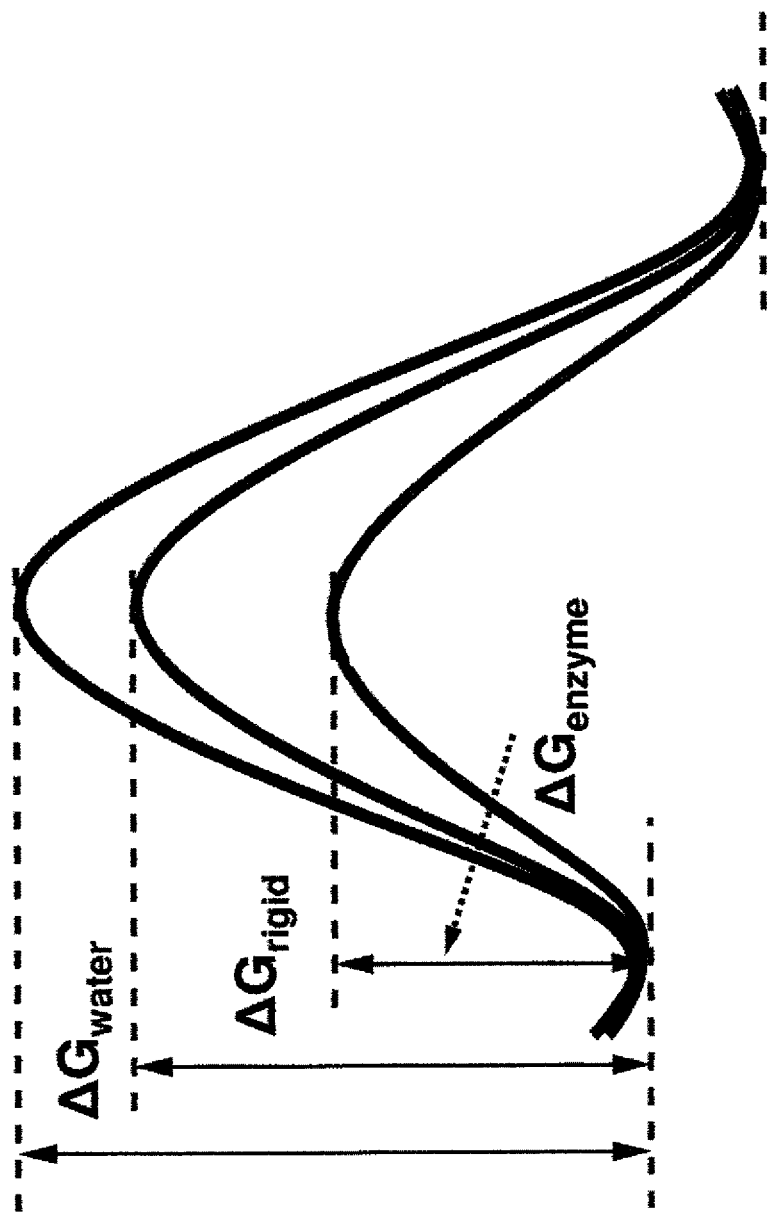
FIG. 13 is a graph illustrating computing the contribution of dynamical and non-dynamical effects. $\Delta G_{water}$ is the reaction in water (no enzyme), $\Delta G_{rigid}$ is rigid enzyme and $\Delta G_{enzyme}$ is free enzyme.

Referring to step 1160 and FIG. 13, the activation energy barrier ($\Delta G$) can also be decreased by the internal protein dynamics, therefore, impacting the enzyme rate kinetics. Therefore, activation energy barrier are expected to be different for reaction in the presence and absence of the enzyme. The effect on the activation energy may be characterized.

Impact of the atomic displacement component on protein reactivity may be identified by making the protein molecule rigid in the an areas of the protein molecule by applying positional restraints proportional to atomic displacements by a factor $\psi$ and by monitoring an impact of the positional restraints on a reaction energy barrier in the constant system energy model. The factor $\psi$ may vary from 0.01 to 100.0, although lesser and greater values of the factor $\psi$ are also contemplated herein. Reaction coordinate distributions across the plurality of protein vibration modes may be compared for a constant value of the factor $\psi$.

Figure 1:
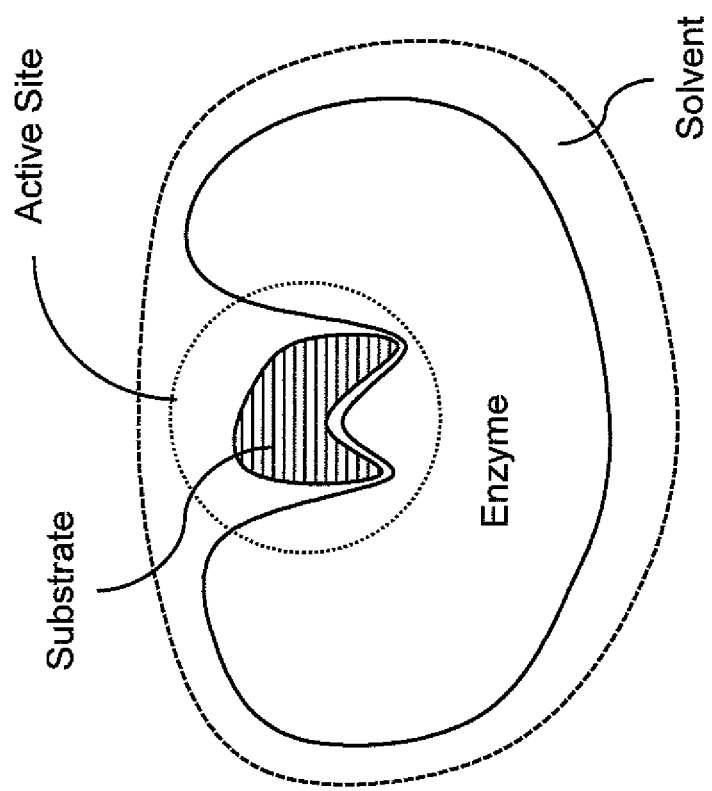
FIG. 1 is a schematic representation of an enzyme showing the active-site (circled), the region where the substrate binds and is converted into product. The enzyme-substrate is surrounded by the solvent.
Figure 2:
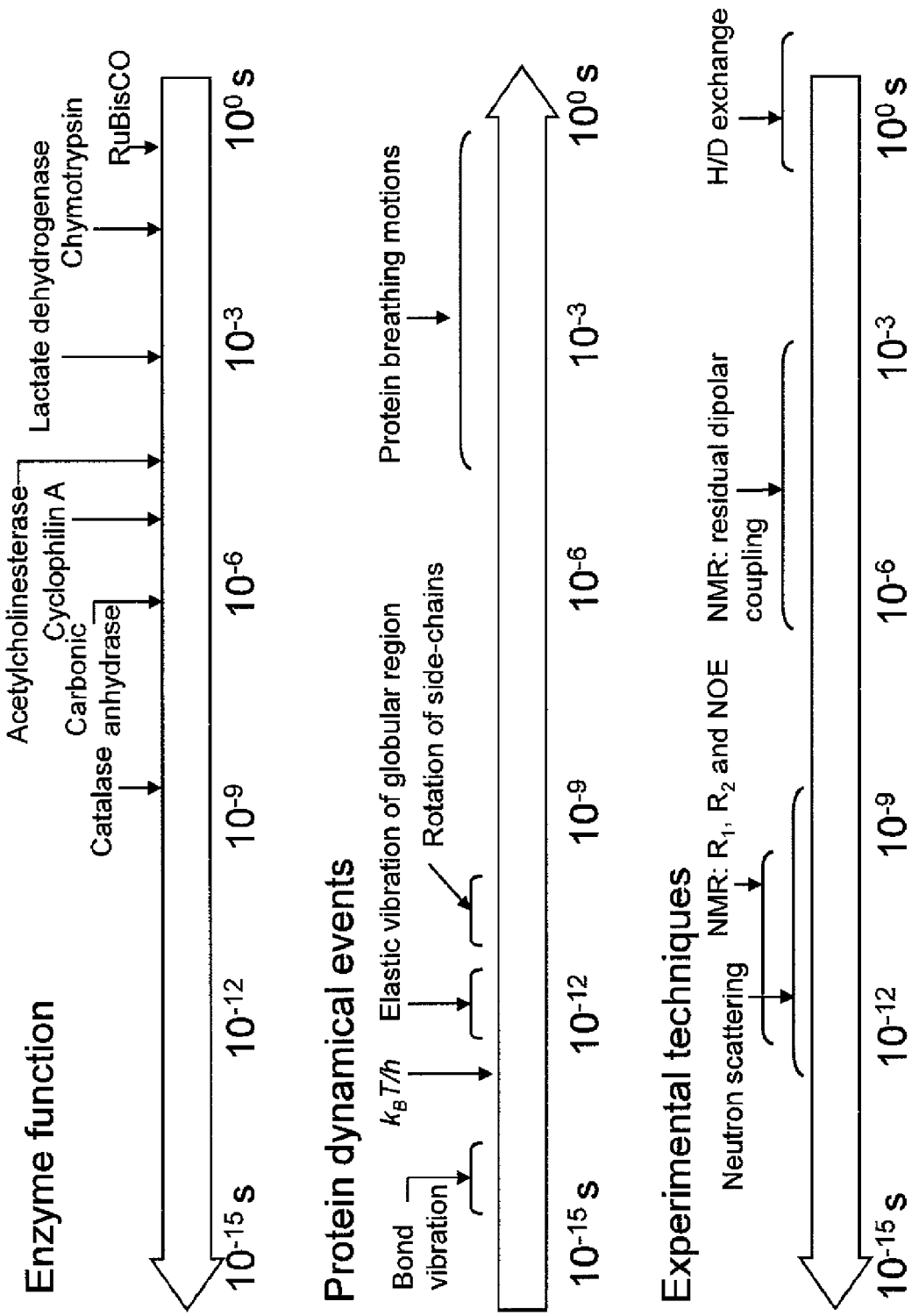
FIG. 2 illustrates how the range of time-scales involved in enzyme catalysis and protein dynamics are similar. The top scale shows the range of substrate turnover steps catalyzed by various enzymes; the middle scale indicates the range of protein motions, while a few selected techniques used to investigate the protein motions are listed on the bottom scale.
Figure 3:
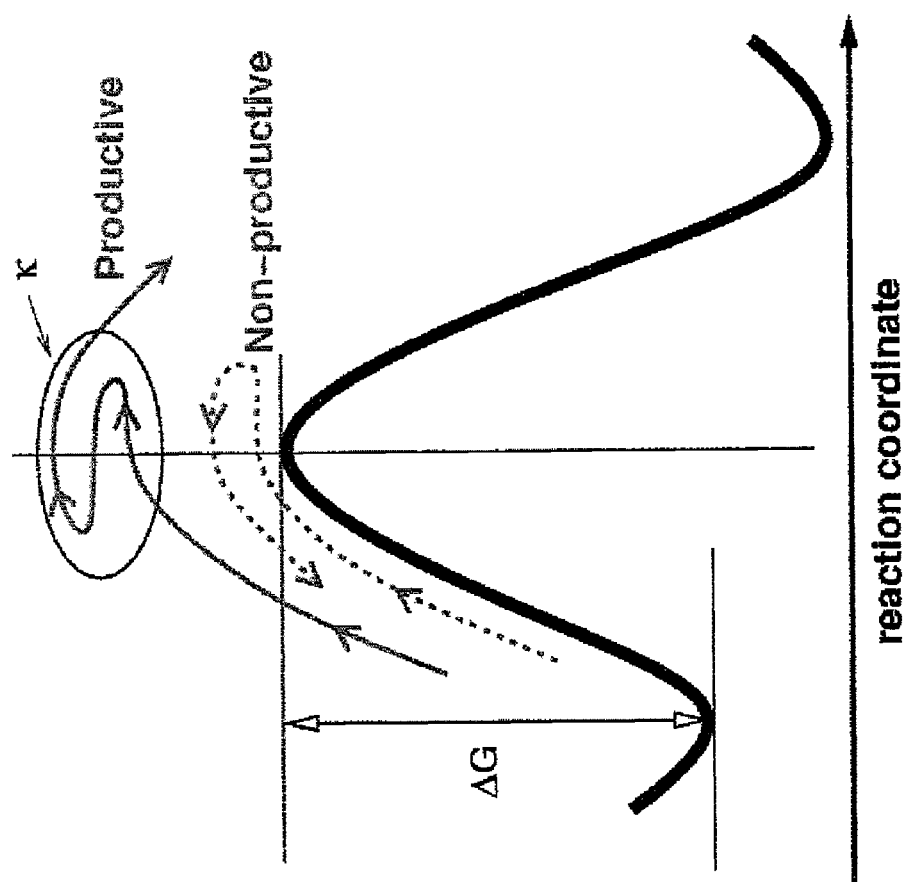
FIG. 3 illustrates a schematic representation of the Transition State Theory (TST) framework that is used to model enzyme activity. In the TST framework, the overall rate ($k_{obs}$) is a product of the equilibrium TST rate constant ($k_{TST}$) and transmission coefficient ($\kappa$). Protein dynamics can influence reaction in two possible ways; by altering the activation free energy barrier ($\Delta G$) and $\kappa$.
Figure 4:
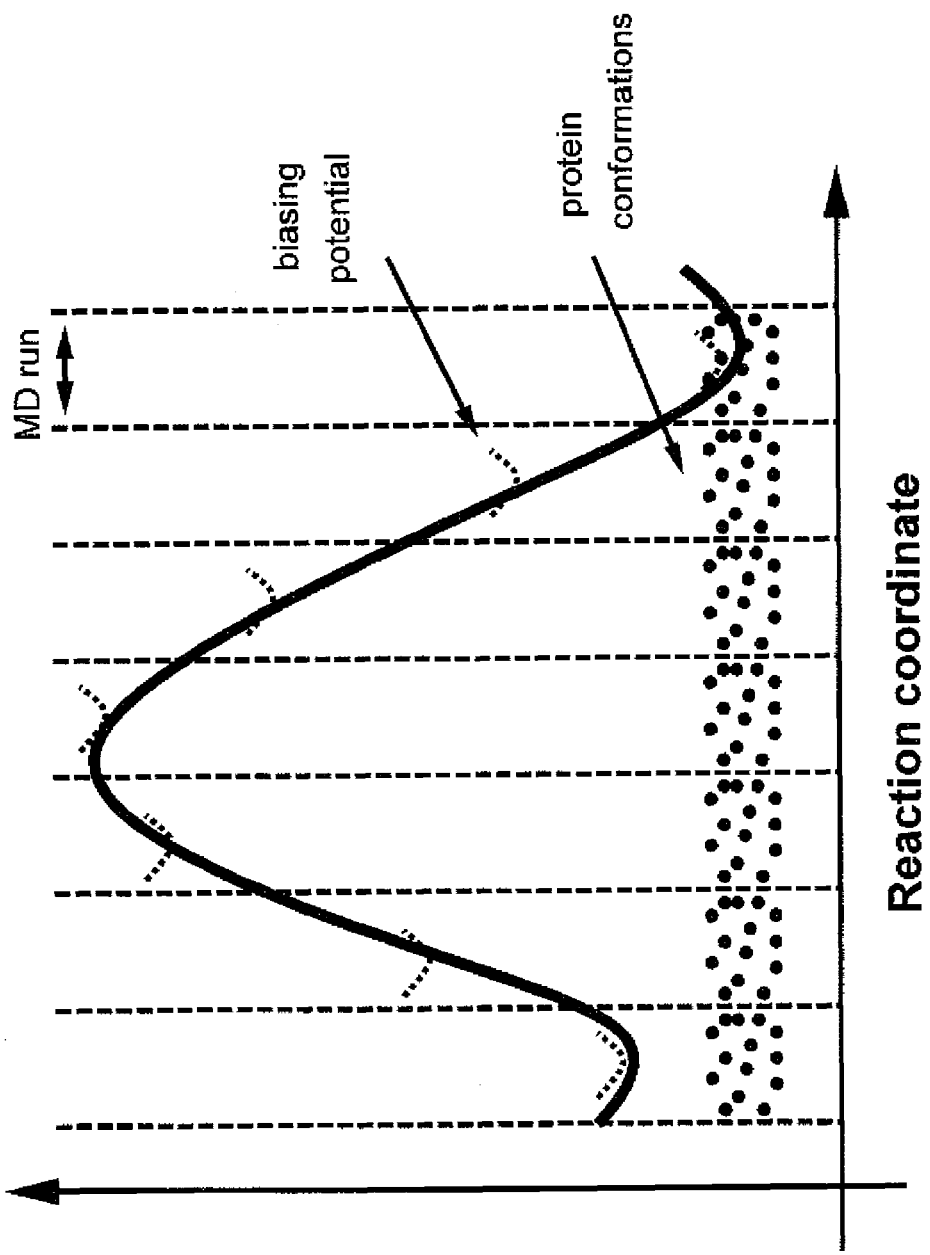
FIG. 4 illustrates the methodology for collecting protein conformational along the reaction profile using umbrella sampling methodology (with the biasing potential). A number of molecular dynamics (MD) runs can be combined for different areas of the reaction coordinate. The regions of energy higher are sampled with application of biasing potential. The entire set of protein conformational sampled are used for computation of the protein vibration modes.
Figure 5:
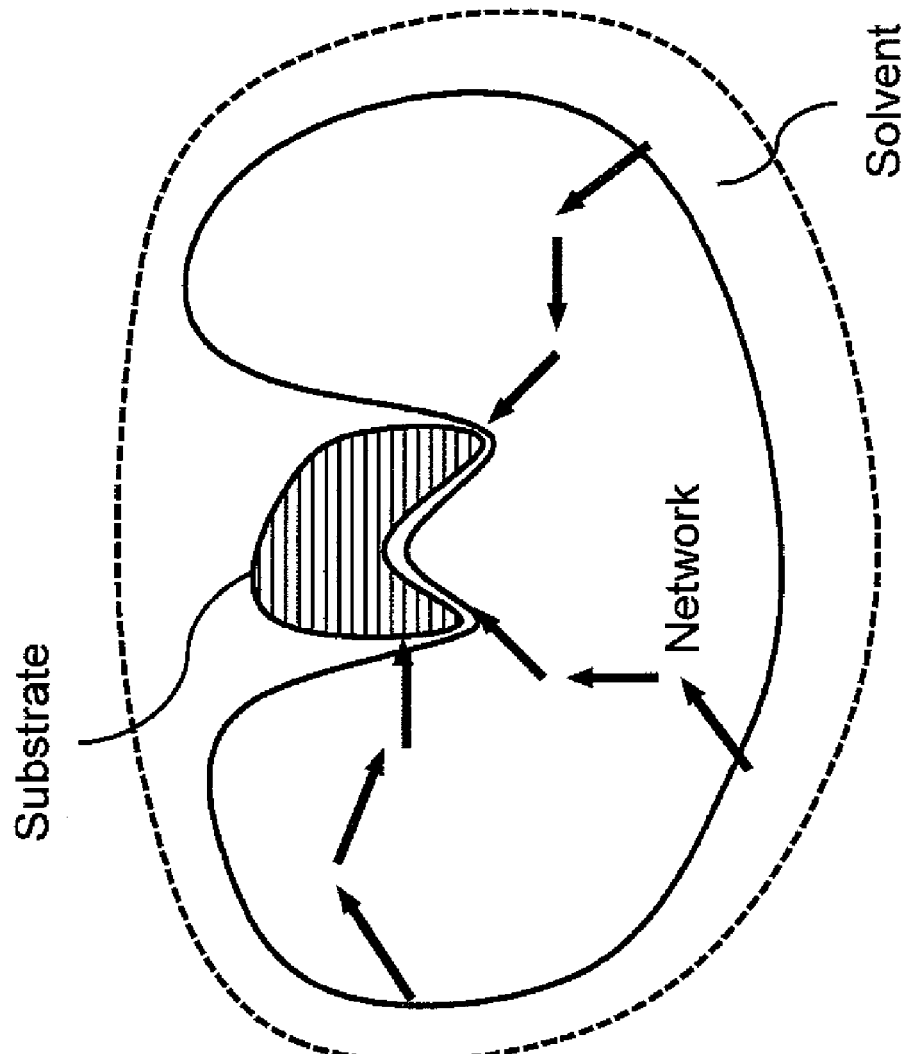
FIG. 5 depicts the integrated view of enzyme and solvent structure, dynamics and function. Enzyme structure outside the active-site plays an important in enzyme mechanism. Network of protein motions/vibrations connect the dynamics regions on the enzyme surface to the active-site. The networks provide pathways for transfer of energy from the solvent to overcome the activation energy barrier.
Figure 6:
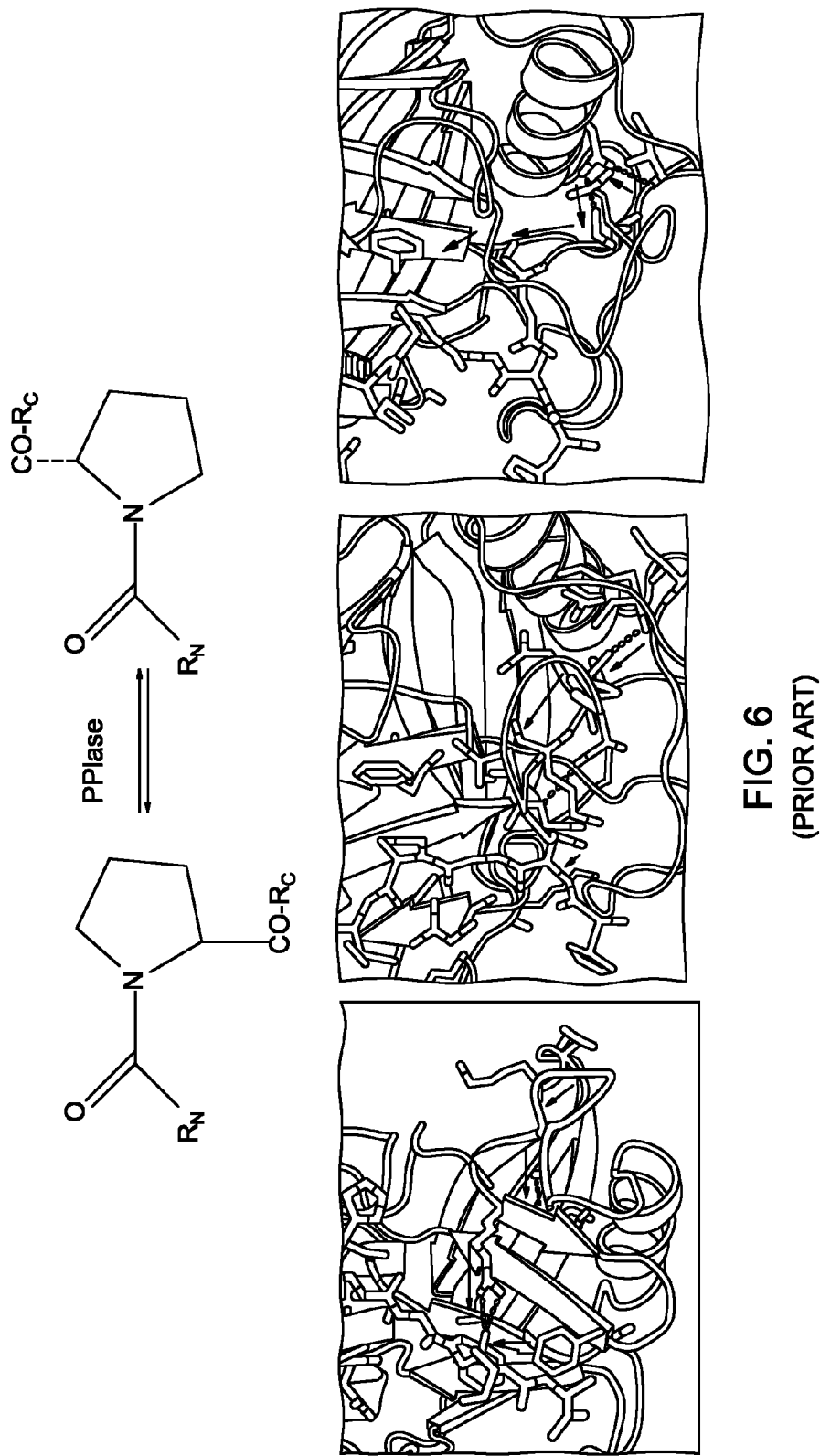
FIG. 6 depicts the cis/trans peptidyl-prolyl isomerization (PPIase) reaction catalyzed by enzyme cyclophilin A and the network of protein vibrations identified in cyclophilin A that promotes the catalytic step of the PPIase reaction. Arrows indicate the interactions from surface loop regions all the way to the active-site. The three alternate pathways in the network were based on the characterization of the reaction coupled vibration modes.
Figure 7:
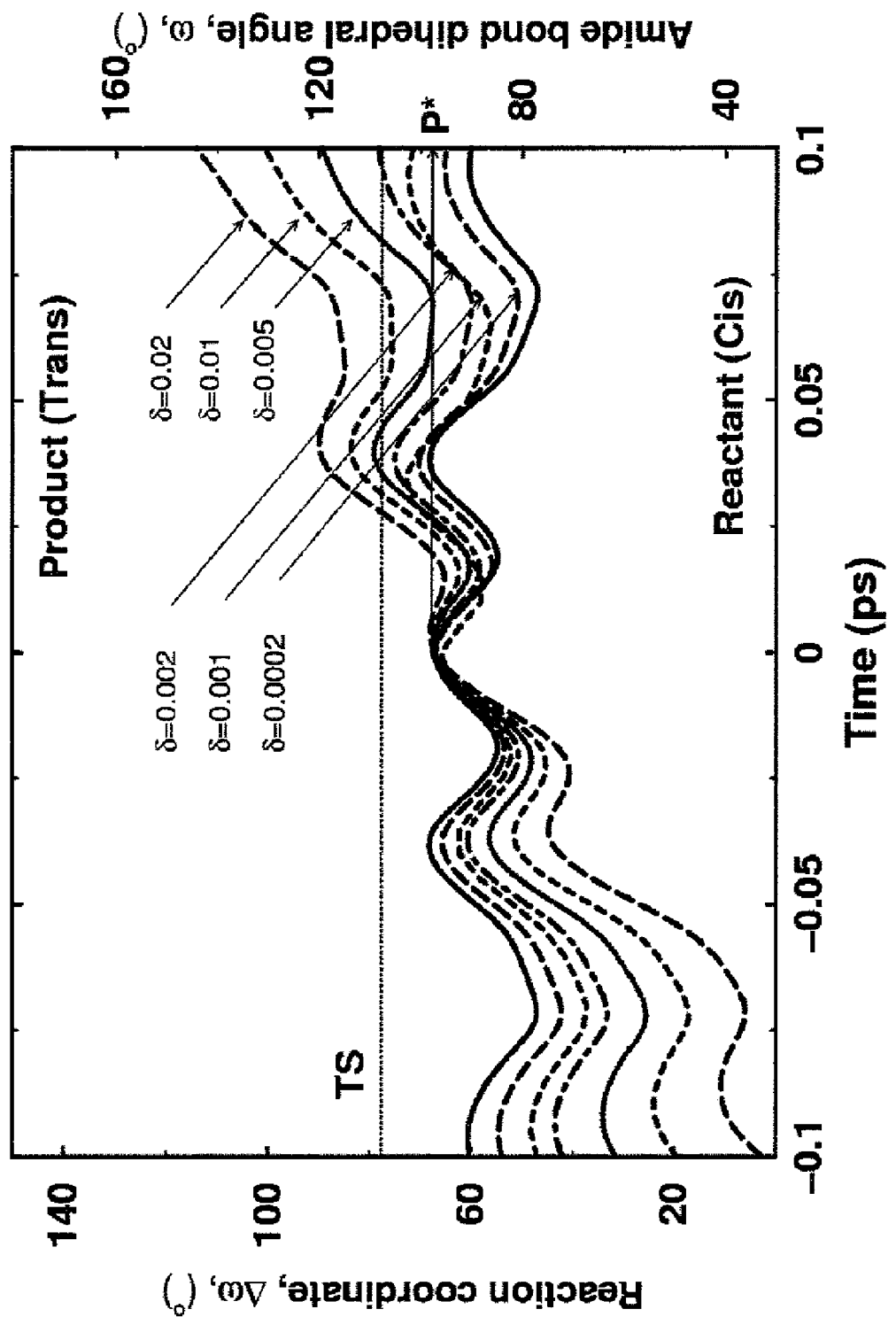
FIG. 7 depicts the effect of reaction promoting protein vibrations on transmission coefficient ($\kappa$). Cyclophilin A studies indicate that increasing additional kinetic energy (ranging between 0.02%-2.0% of total system energy) in protein vibration mode, associated with the network, have a significant impact on the TS barrier recrossings, therefore, $\kappa$.
Figure 8:
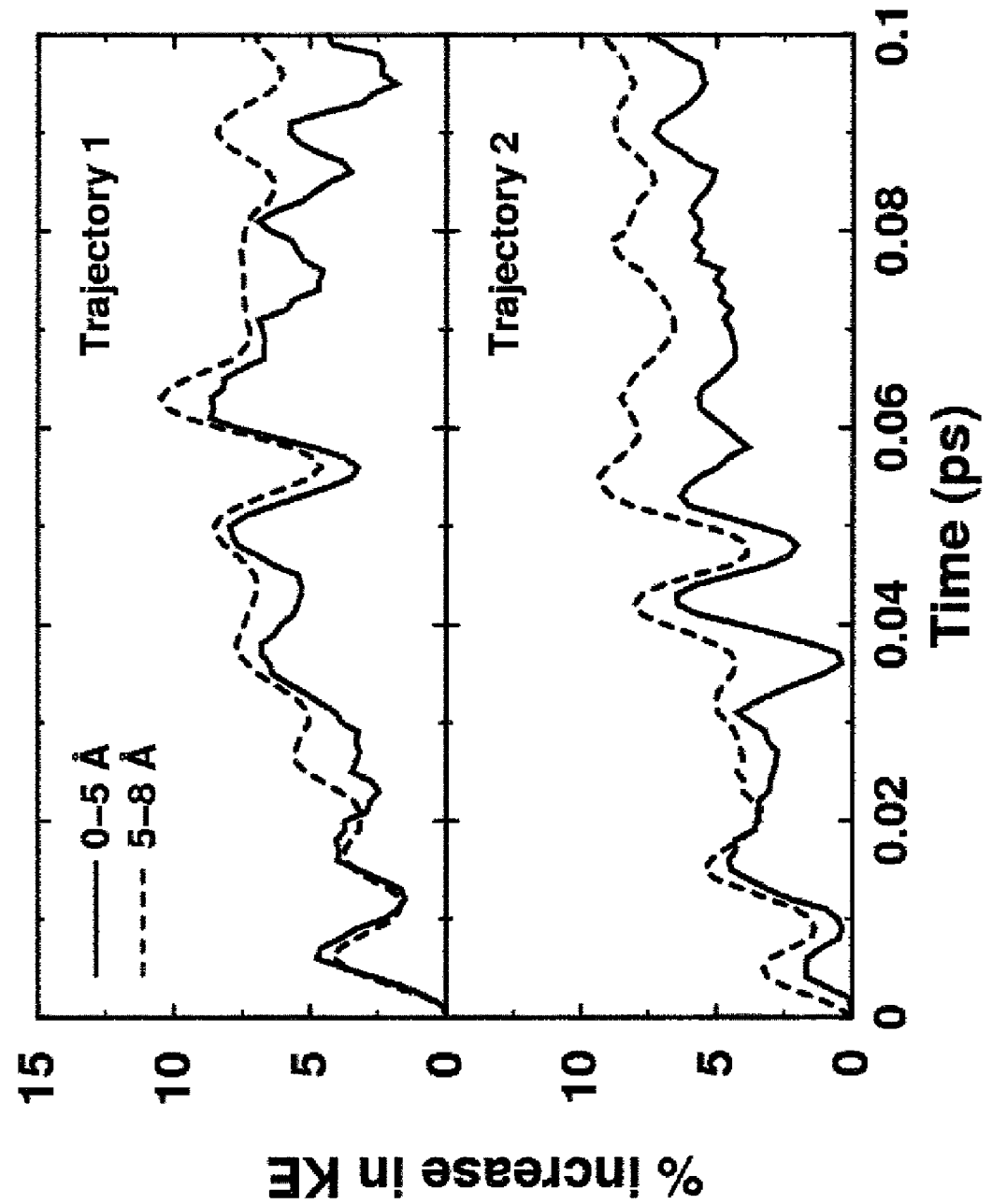
FIG. 8 shows graphs illustrating the effect of additional kinetic energy (KE) in first solvation shell. The KE is transferred from the solvent to the protein residues, as indicated by increasing energy in the protein regions.
Figure 9:
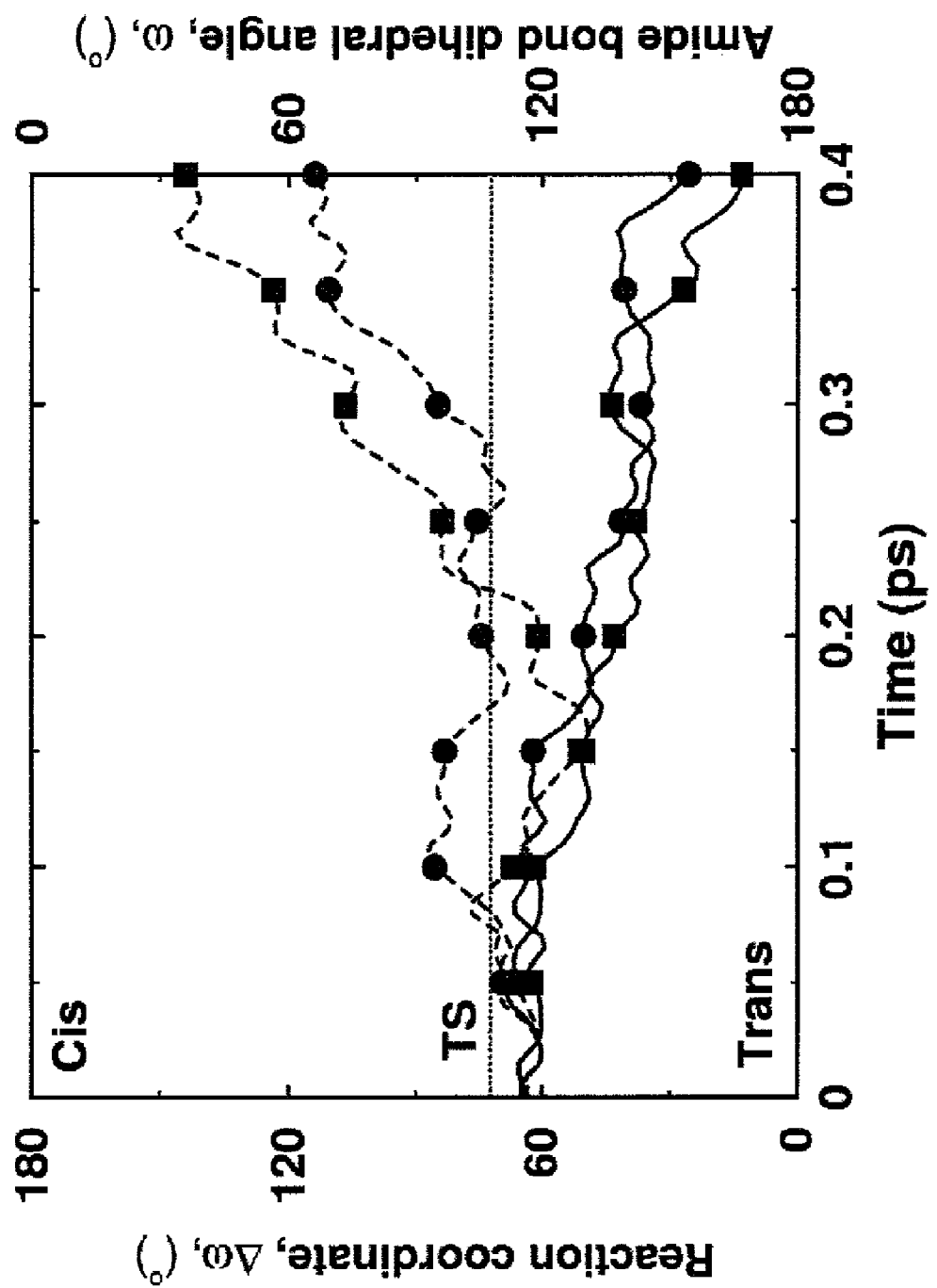
FIG. 9 depicts the impact of energy transfer from solvent to the residues in the network of protein vibrations. Two otherwise non-productive regular trajectories (solid lines) become productive (broken lines) due to transfer of energy from the solvent to residues forming parts of the protein vibrations network.

Referring to step 1170, enzymes are dynamical systems, which have an impact on reaction rates by altering the active-site environment such that more trajectories become productive after successful barrier crossing. For example FIG. 3, illustrates the behavior of two reaction trajectories close to the transition state (TS). The first trajectory returns to the reactant side (non-productive), while the second trajectory crosses the barrier several times before reaching the product state productive). Transmission coefficient ($\kappa$) is a pre-factor which corrects the TST reaction rate for the number of barrier re-crossings. The effect on the transmission coefficient may be characterized.

A velocity component $v^n_{i\alpha}$ for an i-th atom in the system along a Cartesian coordinate direction a after the addition of the scalar is given by:

$$v^n_{i\alpha} = (1-\delta)^{1/2} \times v_{i\alpha} + \eta \times \phi_{i\alpha},$$

wherein $v_{i\alpha}$ is a velocity component for the i-th atom in the system along the Cartesian coordinate direction a prior to the addition of the scalar in an unperturbed state, wherein $\eta$ is a normalization parameter, and $\phi_{i\alpha}$ is an atomic displacement component of the i-th atom along the Cartesian coordinate direction a in the one of the plurality of protein vibration modes for each value of i in the system and for each the Cartesian coordinate direction $\alpha$ which may be an x-direction, an y-direction, or a z-direction. $\delta$ is a constant factor in the range from 0 to 1, and wherein said constant factor represents a fraction of kinetic energy that is imparted to said protein vibration mode. Reaction coordinate distributions across the plurality of protein vibration modes may be compared for a same value of the constant factor.

Collectively, the impact of protein dynamics gives rise to the rate-enhancement achieved by the enzyme. Enzyme rate-enhancement refers to the rate of chemical reaction in the presence and absence of the enzyme. Enzyme facilitates the increase in reaction rate by an effective decrease in the activation energy barrier ($\Delta G$) as well as increase in the number of reactive trajectories successfully crossing over to the product side (increase in the transmission coefficient, $\kappa$). As FIG. 13 depicts the role of protein dynamics on $\Delta G$ can be characterized by making the enzyme rigid (proportional) to the displacements in the protein vibrational modes. It can be expected that the $\Delta G_{rigid}$ for the rigid enzyme and the $\Delta G_{enzyme}$ for the free enzyme will be different, where the $\Delta G_{rigid} - \Delta G_{enzyme}$ providing an estimation of the energy transfer facilitated by the enzyme into the active-sites. The role of the conserved protein vibrations are to facilitate the transfer of energy from the solvent surrounding the protein to the active-site, where it is used to overcome the reaction barrier. The ratio: $\Delta G_{water}/\Delta G_{enzyme}$ provides an estimation of the reaction rate-enhancement, with conversion of enzyme rates as described above in text associated with FIG. 3

In one example, novel methods for the control of motions of individual amino acid residues in a protein are provided, thereby controlling the motions of proteins. In one example, the methods contemplate control of those motions that control the flow of energy in the protein, e.g. enzyme. This can be done by activating, i.e. adding energy to, dynamically active residues in the protein. These residues may be located in the active site of the protein, e.g. enzyme. Alternatively, these residues may be located outside of the active-site of the protein, e.g. enzyme.

Alternately, it is possible that, in order to increase the speed of an enzymatic reaction, there is a need to feed, i.e., deliver, energy into the active-site of the enzyme. In other words, to increase the rate of an enzymatic reaction, it is possible to apply excess energy to the enzyme. In one example, this excess energy is then transferred to the active-site of the enzyme, thereby increasing the rate of catalysis.

In the course of research leading to the present invention, evidence from a diverse family of dinucleotide binding Rossmann fold protein (DBRP) enzymes that catalyze hydride transfer has shown that the regions of high flexibility on the surface are connected by network to the active-site. Even though these diverse enzymes have very different sequence and structures. However, the mechanism of energy transfer between the solvent and the active-site is remarkably similar and well preserved. Therefore, benefits of better understanding enzyme folds and dynamics include the potential for improving the efficiency of microbial factories by modifying and engineering of enzymes, as well as designing new enzymes with novel functionalities. The present invention provides compounds and methods for facilitating these objectives.

Figure 14:
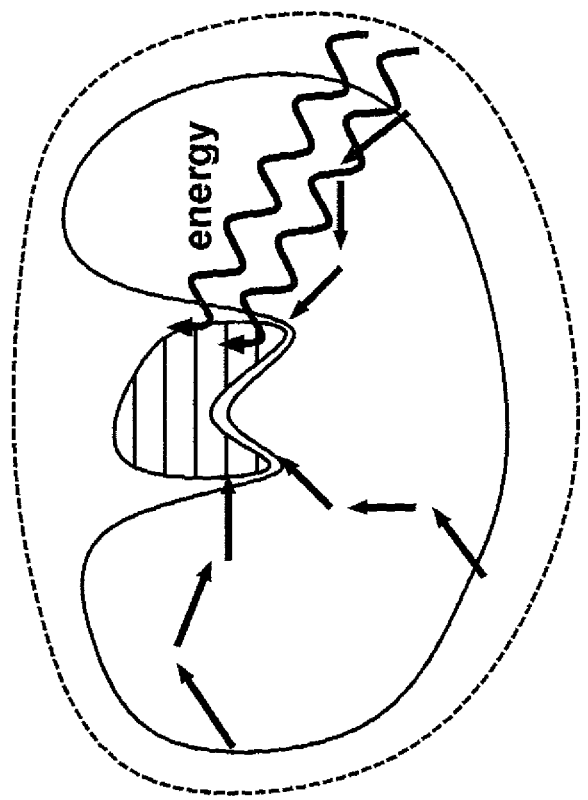
FIG. 14 depicts the pathways of increased energy flow through the network into the enzyme active-site.

Referring to FIG. 14, the present invention provides compositions and methods that have wider significance in the fields of enzyme chemistry, and protein engineering. Identification of the pathways of energy flow as well as modification that enable channeling of energy through these networks to rapidly overcome the reaction barrier and increase in transmission coefficient will lead to designing more efficient enzymes with better rate kinetics. Fundamental understanding of the detailed mechanism of the enzyme catalysis and factors that contribute to the rate-enhancement have implications for understanding the kinetics of biochemical processes. The first reported evidence for a direct link between enzyme catalysis coupled protein dynamics and reaction rate-enhancement is provided. With the new detailed understanding of enzyme function, it may be possible to design more efficient and new enzymes for potential uses in medicine. Further, the insights of dynamical correlations between protein structural elements will provide an alternate view explaining allosteric and cooperative effects in enzyme function (Bouvignies et al, 2005, *Proc. Natl. Acad. Sci. USA* 102: 13885-13890). Therefore, discovered networks of promoting motions/vibrations according to the present invention have wide implications for enzyme engineering and rational protein design.

The identification of non active-site regions in proteins that have an impact on protein activity can lead to better protein engineering. It is contemplated that the methods of the present invention can lead to the creation of more efficient enzymes and also new enzymes with novel functionalities, e.g., through mutational approaches as well a combination of protein fold with right energy pathways in combination with the active-site residues that protein the chemical environment suitable for the desired chemistry. Moreover, structural modifications to improve the energy transfer between various protein parts can lead to better energy transfer, thereby providing better enzyme activity.

For example, an activator molecule may be attached to a protein such as an enzyme. The activator(s) can be used for adding energy to the identified dynamically active residues in the protein. For example, it is possible to attach one or more activator molecules for the control of the vibration mode of one or more amino acid residues of an enzyme. Attachment of activator molecules(s) thus modifies the enzyme. The modification results in increase of the vibration mode of the amino acid residue, ultimately resulting in enhanced enzymatic activity.

Figure 15:
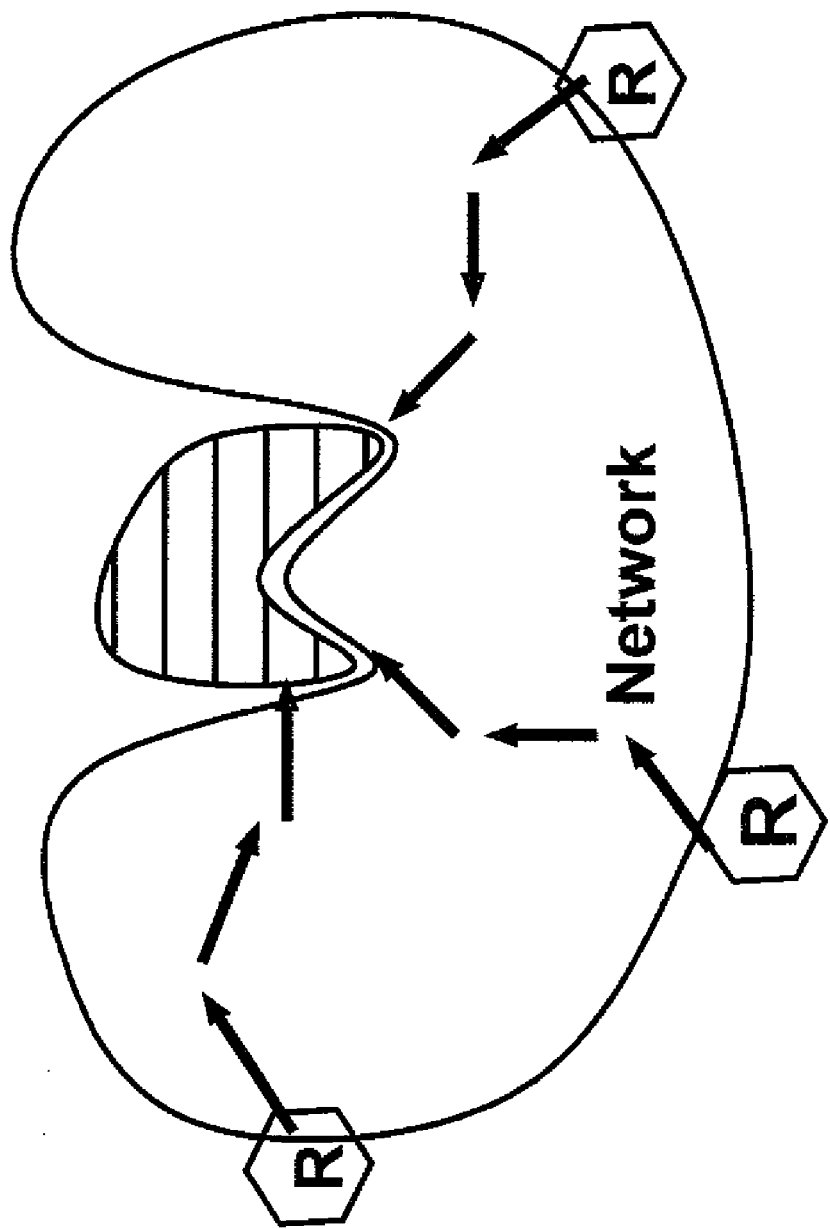
FIG. 15 depicts the schematic of modifying an enzyme by attaching a photo-activated compound to the enzyme. The sites are located on the surface (indicated by R) where the network of protein motions/vibrations shows high flexibility in residues or loops to interaction with the solvent.

Referring to FIG. 15, a schematic of modifying an enzyme is illustrated in which a photo-activated compound is attached to an enzyme at one or more positions depicted as "R". Once the photo-activated compound is stimulated using particular light, energy is transferred (added) to the dynamically important residue, resulting in transfer of kinetic energy by the network, and ultimately enhancing the catalytic reaction that takes place in the active-site of the enzyme.

In general, compositions and methods are disclosed which can lead to protein engineering of moieties such as large structures like flexible loops and strands within the protein as well as smaller structures like branched alkyl or inorganic chains, that are especially well adapted as energy transmitting modifications. Conversely, engineering modification that would increase the rigidity would lead to decreased dynamical effects. Examples of such modifications include disulfide-bridges and other covalent/non-covalent interactions based cross-linking of protein regions.

Experimental data has been generated from theoretical and computational modeling of different classes of enzymes that reveal that protein dynamical events that participate in promoting the enzyme reaction are conserved over evolution. These intrinsic protein dynamical events occur through a network of protein residues and hydrogen-bonds and hydrophobic interactions that are conserved from species ranging from bacteria to human. The methods used for these studies include generation of free energy profile from classical molecular dynamics simulation with umbrella sampling, quasi-harmonic analysis and structural analysis.

For example, steps in the flow chart of FIG. 11 may be employed to identity the dynamically active residues in a network. However, not all of these steps have to be used to identify dynamically active residues. Once the network is identified computationally or experimentally, kinetic energy is added to the modes or protein residues in the network and the impact of reaction is observed. It has already been demonstrated (Agarwal, 2005, *J. Am. Chem. Soc.* 127: 15248-15256) that addition of kinetic energy in select protein vibrations or solvent around the network residues leads to acceleration in the reaction.

There are multiple pathways of energy transfer in the protein. Each pathway itself may involve two or more amino acid residues. The multiple pathways provide robustness to the enzyme to perform its designated function. Simply put: alternate pathways allow more energy to be collected from the solvent by multiple network residues on the protein surface, which increase the area of interaction with the solvent. Therefore, a minimum of one residue needs to be modified. However, it is expected that multiple residue may offer the most benefit.

Figure 16:
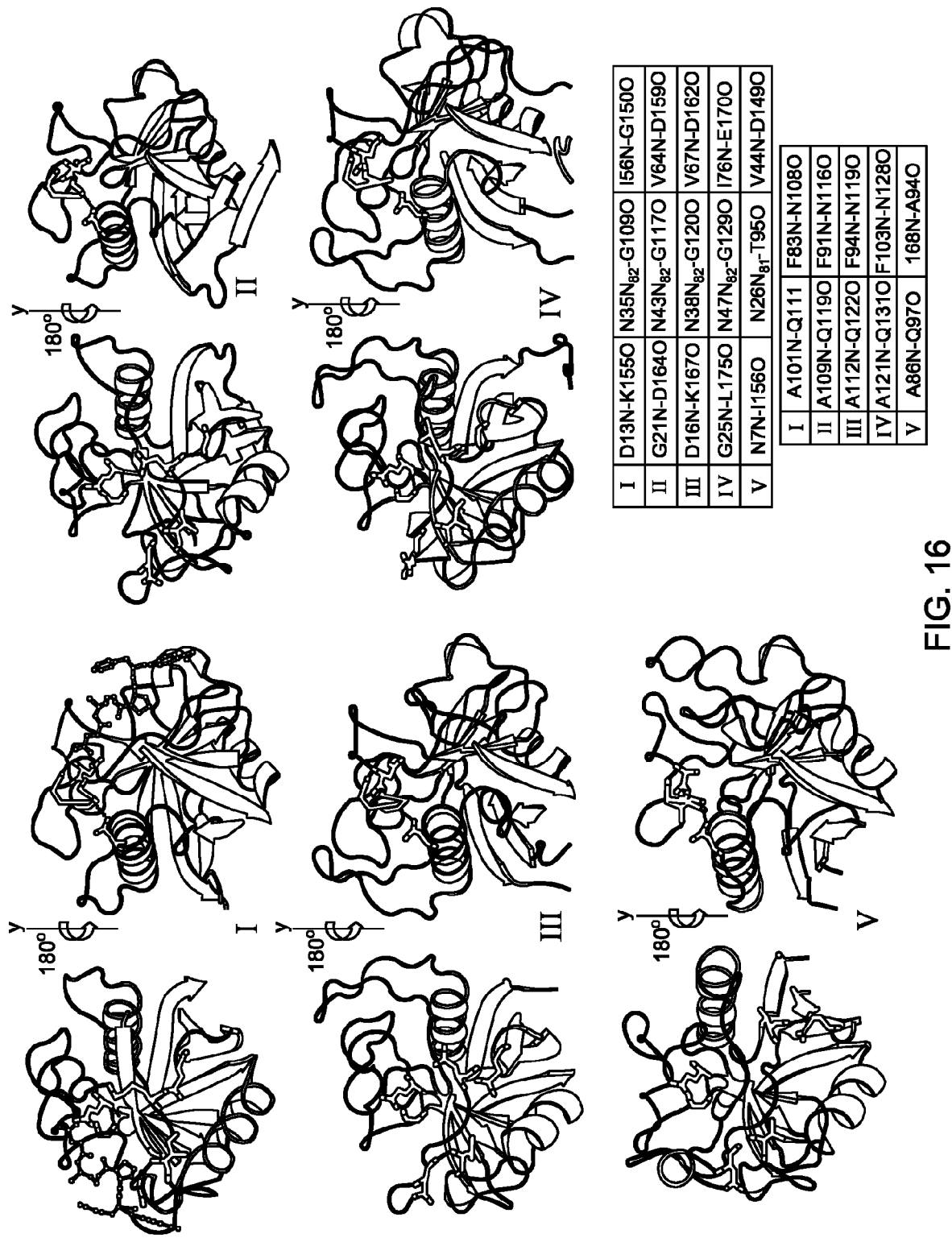
FIG. 16 depicts conservation of the network of function promoting protein vibrations as a part of PPIase fold: human cyclophilin A (I) PDB code: 1RMH; human cyclophilin B (II) PDB code: 1CYN; B. Malayi (III) PDB code: 1A33; B. Taurus (IV) PDB code: 1IHG; E. coli (V) PDB code: 2NUL. Table lists the conserved network residues and interactions. Even though the sequences show considerable variability but the interaction at the location is conserved.

Referring to FIG. 16, the present invention provides examples of conservation of network for energy flow in the enzyme cyclophilin A. Enzyme cyclophilin A is involved in many biological reactions including protein folding and intracellular protein transport. It is a ubiquitously expressed cytosolic protein, and is the major intracellular receptor protein for the immunosuppressive drug cyclosporin A. Cyclophilin A is a peptidyl-prolyl cis/trans isomerase (PPIase), which catalyzes the isomerization of peptidyl-prolyl amide bonds, which are N-terminal to proline residues in a wide variety of peptides and protein substrates. Cyclophilin A is required for the infectious activity of HIV-1. Additional systems like dihydrofolate reductase have also shown presence of similar networks (see below). Collectively these examples important provide information for the link between structure and internal dynamics during the chemical steps catalyzed by these enzyme systems. Computational modeling was used to identify internal protein dynamics that plays role in promoting the catalytic step. For each of these enzymes the investigations were performed on structures from several species ranging from bacteria to human, with low sequence homology ranging from 28-35%. The identified protein dynamical events were analyzed for identification and location of the displacements within the protein structure. The results show that for these enzyme systems catalyzing chemically different reaction the dynamical events that are coupled, and are promoting the reactions, are conserved over evolution. Moreover, the network (or networks) of protein motions/vibrations formed by interactions that range from surface loop regions all the way to the active-site, are completely conserved.

Computational studies were performed with the following enzymes: 1. Cyclophilin A from 3 different species including *Bos taurus* and *Plasmodium yoelli* and human, and using 4 different substrates; 2. Dihydrofolate reductase from 4 different species including *Escherichia colt Candida albicans, Mycobacterium tuberculosis* and human; 3. Ribonuclease A from 3 different species including *Bos taurus, Rattus norvegicus* and *Rana catesbeiana;* 4. Cellulase (Cel9A) from *Thermobifda fusca*. Thus, in a variety of enzymes, the presence of networks of protein vibrations promoting enzyme function have been identified. What that implies is the identification of vibrations whose function is to provide energy to the reaction. Manipulation of these vibrations through adding or removal of the energy can therefore impact the enzyme kinetics. It is contemplated that the methods of the present invention are generally applicable to all proteins, and in particular is applicable to enzymes.

Figure 17:
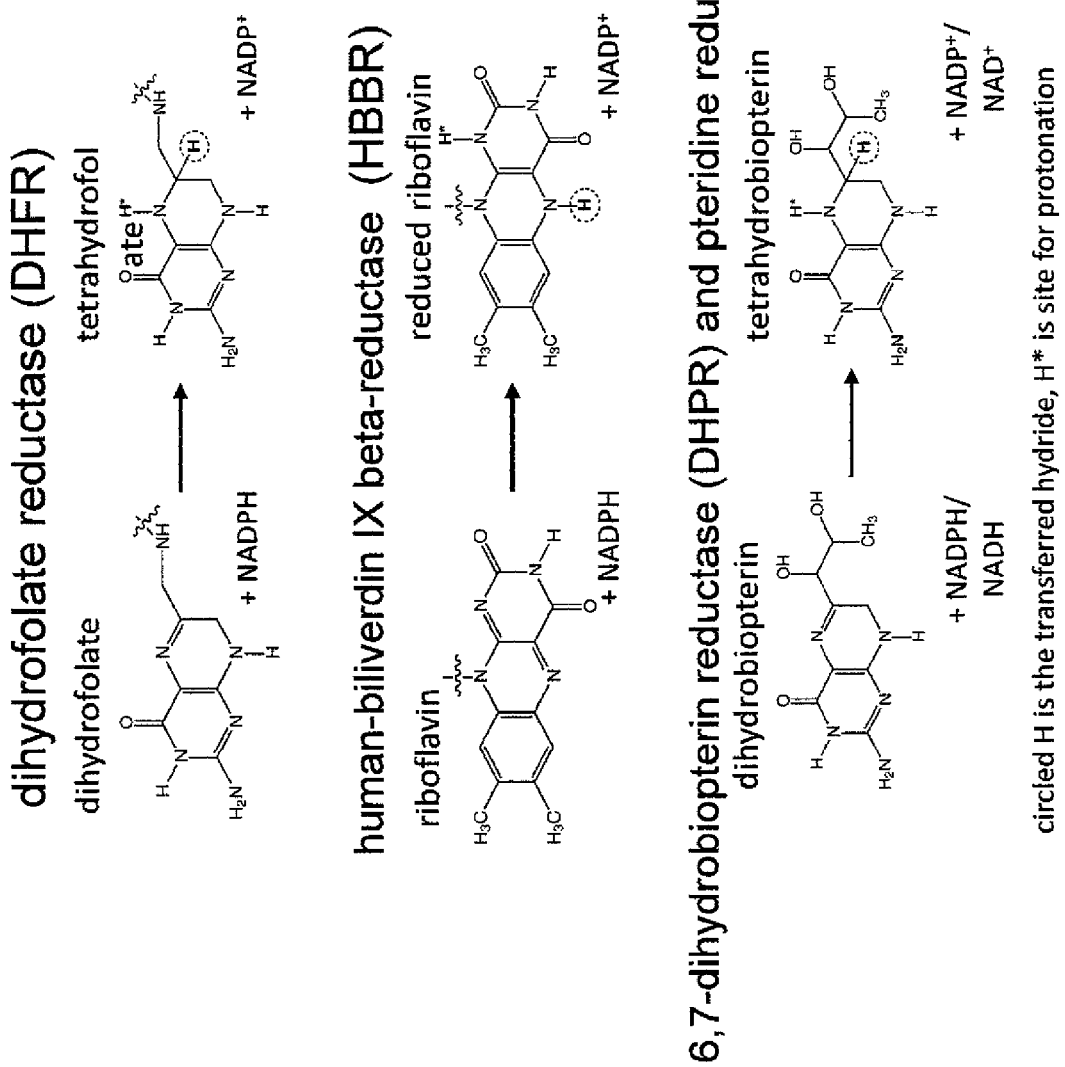
FIG. 17 depicts the biochemical details of the dinucleotide binding Rossmann fold protein (DBRP) enzymes that catalyze hydride transfer: dihydrofolate reductase (DHFR)

Referring to FIG. 17, the methods disclosed herein can also be used to lead to interesting insights into the evolution of protein structure and enzyme families. Using statistical mapping of interactions in proteins to discover coevolved residue sites, it is possible to provide evidence of long-range communication between distant sites. These insights are consistent with the emerging view of protein dynamics as a contributing factor to long-range interactions. An additional area of importance is the understanding into the evolution of enzyme super-families. Structural and genomic analysis of mechanistically diverse set of enzymes that share common protein fold have provided evidence that a wide range of chemical reactions, which share common mechanistic steps, share overall protein fold and individual residues have been optimized for the particular reaction. It is possible that the enzyme structure has also been optimized over evolution for the dynamical contribution to catalysis. Therefore, knowledge of protein dynamics in enzyme catalysis is also important for understanding the defining characteristics of enzyme super-families.

Referring to FIG. 18, the mechanism of energy implication also has important implication for rational protein design. It is known that enzymes catalyzing the same reactions belong to a protein fold family, where the overall characteristic shape of the protein is similar. Also, enzymes catalyzing mechanistically similar reactions often belong to the same super-family of protein fold. This example illustrated through the identification of dynamical regions of importance in the diverse super-family of DBRP enzymes. Even in structurally diverse enzymes dynamically active regions marked as A, B and C are conserved due to their role in the enzyme catalysis. These regions may provide practical example of sites in the enzyme for the attachment of activator for alternate of the enzyme activity According to an aspect of the present invention, a protein molecule with a potential for enhancement of a chemical reaction rate may be identified. The method includes identifying a plurality of dynamically active residues in each of multiple species of protein molecules based on a set of protein vibration modes; calculating dynamic cross-correlation factors at a time scale of interactions among the plurality of dynamically active residues; analyzing the interactions among each of the multiple species of protein molecules; identifying a protein vibration network that conserves the interactions above a level of magnitude among the multiple species of protein molecules; and determining whether the protein vibration network is present in each of the multiple species of protein molecules. Each protein vibration mode in the set may be selected based on a degree of overlap of a reaction coordinate distribution with a reaction coordinate range of a catalytic reaction of a protein molecule among the multiple species of protein molecules.

The activator may increase energy transferred into the active site by alteration of a physical structure in a surface loop region of the modified protein thereby increasing coupling of energy with a solvent. The alteration may include an increase in a length of the surface loop region.

The dynamically active residue may be located directly on an active site of the prototype protein. Alternately, the dynamically active residue is located outside an active site of the prototype protein.

According to an aspect of the present invention, a modified protein is provided, which includes: a prototype protein including a dynamically active residue located outside of an active site of the prototype protein and an activator attached to the dynamically active residue. The activator modifies a magnitude of atomic displacement of atoms in a protein vibration mode. The modified magnitude of the atomic displacement alters a chemical reaction rate of a reaction mediated by the modified protein relative to a chemical reaction rate mediated by the prototype protein in the absence of the activator.

The activator may be covalently bonded to the dynamically active residue. In one example, the dynamically active residue may be an amino acid derivative.

The activator may include a photo-activated group for transferring kinetic energy to the active site. For example, the activator may include an azobenzene group that induces a mechanical change in a surface loop region in the prototype protein.

FIG. 19 depicts a chemical modification that allows practice of the invention by enabling activation of the enzyme with photo-activated compounds containing the azobenzene chemical group. This group of compound can adopt either the trans or the cis conformation and this change can be induced by light. This can be used to make modification to peptide to induce photo-activated conformational changes (Bredenbeck et al., "Picosecond conformational transition and equilibration of a cyclic peptide," (2003), *Proc. Natl. Acad. Sci. USA*, 100: 6452-6457). Further the energy from the light is transferred into the protein through conformational changes. Making the chemical modification on the flexible surface loop regions that form the network of protein motions will allow directing energy into the active-site.

Referring to FIG. 20, an exemplary apparatus for utilizing a modified protein is shown according to the present invention. The exemplary apparatus includes an opaque container 2010 that provides a sealed environment. The opaque container 2010 may have a passivated inner surface to prevent corrosion. A modified-protein containing solution 2020 is placed in the opaque container 2010. A monochromatic lamp 2030 emitting monochromatic electromagnetic radiation is provided within the opaque container, which activates a photosensitive ligand of a modified protein. The modified protein may be any protein that may be formed by the methods of the present invention as described above. The wavelength of the monochromatic light may be within the visible spectrum, within the infrared wavelength range, or may be with the ultraviolet range. In some cases, the wavelength of the monochromatic light may be within the wavelength range of an X-ray or within the wavelength range of microwaves. In general, the wavelength range of the monochromatic radiation may be from 0.01 nm to 30 cm, and typically from 10 nm to 1 mm. An agitator 2040 may be provided within the opaque container to induce movement of the modified-protein containing solution 2020 within the opaque container 2010. For example, the agitator 2040 may have an axis and fans attached to the axis so that the fans induce rotational movement of the modified-protein containing solution 2020 as the agitator rotates around the axis.

The exemplary apparatus may be employed to alter a reaction rate of a protein. In general, such an apparatus may include an opaque container that holds a solution and including a solvent and a modified protein, wherein the modified protein includes a prototype protein including a dynamically active residue located outside of an active site of the prototype protein and an activator attached to the dynamically active residue and a monochromatic light source contained within the opaque container. The activator modifies a magnitude of atomic displacement of atoms in a protein vibration mode. The modified magnitude of the atomic displacement alters a chemical reaction rate of a reaction mediated by the modified protein relative to a chemical reaction rate mediated by the prototype protein in the absence of the activator. The activator may include a photo-activated group for transferring kinetic energy to the active site. For example, the activator may include an azobenzene group that induces a mechanical change in a surface loop region in the prototype protein.

While the invention has been described in terms of specific embodiments, it is evident in view of the foregoing description that numerous alternatives, modifications and variations will be apparent to those skilled in the art. Other suitable modifications and adaptations of a variety of conditions and parameters normally encountered in molecular biology, protein chemistry, and protein modeling, obvious to those skilled in the art, are within the scope of this invention. All publications, patents, and patent applications cited herein are incorporated by reference in their entirety for all purposes to the same extent as if each individual publication, patent, or patent application were specifically and individually indicated to be so incorporated by reference. Accordingly, the invention is intended to encompass all such alternatives, modifications and variations which fall within the scope and spirit of the invention and the following claims.

What is claimed is:

1. A method of identifying a dynamically active residue that affects a catalytic reaction in a protein molecule, said method comprising:
   identifying a plurality of protein motions that are prevalent during a catalytic reaction mediated by a protein molecule;
   selecting a protein vibration mode from said plurality of protein motions based on a degree of overlap of a reaction coordinate in each of said plurality of protein motions with a reaction coordinate range of said catalytic reaction;
   identifying a dynamically active residue of said protein molecule by performing a computer simulation employing a computer based on said selected protein vibration modes, wherein said protein motions in said protein molecule are computed by identifying protein vibration modes coupled with said catalytic reaction, wherein quasi-harmonic analysis of conformations of said protein molecule along a reaction pathway is employed to identity said protein vibration modes, wherein degree of reactivity of said protein molecule is determined based on dynamical behavior of a reaction trajectory along a reaction pathway of said catalytic reaction, wherein said degree of reactivity is computed by identifying a change in transmission coefficient through said reaction pathway by employing a constant system energy model, wherein a total energy of a system remains constant in said constant system energy model, and wherein each velocity component of atoms in said system is scaled down by a constant factor in a computational model for said constant system energy model, and wherein a scalar that is proportional to an atomic displacement component of each atom in one of said plurality of protein vibration modes is added to each velocity component of each atom in said constant system energy model, wherein impact of said atomic displacement component on protein reactivity is identified by making the protein molecule rigid in the areas of said protein molecule by applying positional restraints proportional to atomic displacements by a factor $\psi$ and by monitoring an impact of said positional restraints on a reaction energy barrier in said constant system energy model; and
   embodying, employing said computer, data representing said identified dynamically active residue of said protein molecule in a non-transitory computer readable data storage medium.

2. The method of claim 1, wherein a velocity component $v''_{i\alpha}$ for an i-th atom in said system along a Cartesian coordinate direction $\alpha$ after said addition of said scalar is given by:

$$v''_{i\alpha} = (1-\delta)^{1/2} \times v_{i\alpha} + \eta \times \phi_{i\alpha},$$

wherein $v_{i\alpha}$ is a velocity component for said i-th atom in said system along said Cartesian coordinate direction a prior to said addition of said scalar in an unperturbed state, wherein $\eta$ is a normalization parameter, and $\phi_{i\alpha}$ is an atomic displacement component of said i-th atom along said Cartesian coordinate direction $\alpha$ in said one of said plurality of protein vibration modes for each value of i in said system and for each said Cartesian coordinate direction $\alpha$ which may be an x-direction, an y-direction, or a z-direction.

3. The method of claim 2, wherein $\delta$ is a constant factor in the range from 0 to 1, and wherein said constant factor represents a fraction of kinetic energy that is imparted to said protein vibration mode.

4. The method of claim 2, further comprising comparing reaction coordinate distributions across said plurality of protein vibration modes in a single protein molecule for a same value of said constant factor.

5. The method of claim 1, wherein said factor ψ varies from 0.01 to 100.0.

6. The method of claim 1, further comprising comparing reaction coordinate distributions across said plurality of protein vibration modes for a constant value of said factor ψ.

7. The method of claim 1, wherein said atomic displacement component of each atom in said one of said plurality of protein vibration modes is calculated employing at least one of normal mode analysis on said protein molecule, principal component analysis on said protein molecule, experimental analysis based on nuclear magnetic resonance (NMR) on said protein molecule, experimental analysis based on X-ray crystallography, and experimental analysis based on neutron scattering on said protein molecule.

8. The method of claim 1, further comprising:
providing a model for a catalytic reaction mediated by said protein molecule including a description of said reaction pathway; and
generating samples of conformations of said protein molecule along said reaction coordinate, wherein said plurality of protein vibration modes are selected among protein vibration modes that are prevalent during said catalytic reaction from said samples of conformations of said protein molecule.

9. The method of claim 1, wherein said protein molecule is an enzyme.

10. The method of claim 1, further comprising identifying protein regions that show a large conformational fluctuation in said protein molecule in said selected protein vibration mode, wherein said dynamically active residue is located in said identified protein regions.

11. The method of claim 1, further comprising:
selecting at least another protein vibration mode from said plurality of protein vibration modes based on said degree of overlap of reaction coordinate distribution in each of said plurality of protein vibration modes with said reaction coordinate range of said catalytic reaction; and
analyzing conformational fluctuation in said protein molecule in said selected protein vibration mode and said selected at least another protein vibration mode, wherein said dynamically active residue is identified by said analyzing of said conformational fluctuation.

12. The method of claim 1, further comprising:
identifying at least another dynamically active residue; and
calculating dynamic cross-correlation factors at a time scale of interaction among said dynamically active residue and said at least another dynamically active residue.

13. The method of claim 12, further comprising:
analyzing said interactions across a multiple species of protein molecules including said protein molecule; and
identifying a protein vibration network of interactions from a surface of said protein molecule to an active site of said protein molecule by which energy is transferred to said catalytic reaction.

14. A method of modifying a chemical reaction rate of a protein-mediated reaction, said method comprising:
selecting a protein vibration mode of a protein molecule based on a degree of overlap of a reaction coordinate distribution with a reaction pathway range of a catalytic reaction;
determining a dynamically active residue on said protein molecule by method of claim 1; and
inducing contact between an activator and said dynamically active residue to modify a magnitude of atomic displacement of atoms in said selected protein vibration mode, wherein said modified magnitude alters said chemical reaction rate of said protein-mediated reaction relative to a chemical reaction rate in the absence of said activator.

15. The method of claim 14, wherein said dynamically active residue is an amino acid derivative.

16. The method of claim 14, wherein said protein molecule is an enzyme and said protein-mediated reaction is an enzymatic activity.

17. The method of claim 14, wherein said activator is attached to said dynamically active residue.

18. The method of claim 14, further comprising:
identifying a plurality of protein vibration modes that are prevalent during said protein-mediated reaction; and
selecting said protein vibration mode from said plurality of protein vibration modes based on said degree of overlap of said reaction coordinate distribution in each of said plurality of protein vibration modes with a reaction coordinate range of said protein-mediated reaction.

19. The method of claim 18, wherein degree of reactivity of said protein molecule is determined based on dynamical behavior of a reaction trajectory along a reaction pathway of said catalytic reaction, wherein said degree of reactivity is computed by identifying a change in transmission coefficient through said reaction pathway by employing a constant system energy model, wherein a total energy of a system remains constant in said constant system energy model, and wherein each velocity component of atoms in said system is scaled down by a constant factor in a computational model for said constant system energy model, and wherein a scalar that is proportional to an atomic displacement component of each atom in one of said plurality of protein vibration modes is added to each velocity component of each atom in said constant system energy model.

20. The method of claim 19, wherein a velocity component $v''_{i\alpha}$ for an i-th atom in said system along a Cartesian coordinate direction a after said addition of said scalar is given by:

$$v''_{i\alpha} = (1-\delta)^{1/2} \times v_{i\alpha} + \eta \times \phi_{i\alpha},$$

wherein $v_{i\alpha}$ is a velocity component for said i-th atom in said system along said Cartesian coordinate direction a prior to said addition of said scalar in an unperturbed state, wherein η is a normalization parameter, and $\phi_{i\alpha}$ is an atomic displacement component of said i-th atom along said Cartesian coordinate direction α in said one of said plurality of protein vibration modes for each value of i in said system and for each said Cartesian coordinate direction α which may be an x-direction, an y-direction, or a z-direction.

21. The method of claim 20, wherein δ is a constant factor in the range from 0 to 1, and wherein said constant factor represents a fraction of kinetic energy that is imparted to said protein vibration mode.

22. The method of claim 21, further comprising comparing reaction coordinate distributions across said plurality of protein vibration modes for a same value of said constant factor.

23. The method of claim 18, wherein impact of said atomic displacement component on protein reactivity is identified by making the protein molecule rigid in the an areas of said protein molecule by applying positional restraints proportional to atomic displacements by a factor ψ and by monitoring an impact of said positional restraints on a reaction energy barrier in said constant system energy model.

24. The method of claim 23, wherein said factor ψ varies from 0.01 to 100.0.

25. The method of claim 24, further comprising comparing reaction coordinate distributions across said plurality of protein vibration modes for a constant value of said factor $\psi$.

26. The method of claim 18, wherein said atomic displacement component of each atom in said one of said plurality of protein vibration modes is calculated employing at least one of normal mode analysis on said protein molecule, principal component analysis on said protein molecule, experimental analysis based on nuclear magnetic resonance (NMR) on said protein molecule, experimental analysis based on X-ray crystallography, and experimental analysis based on neutron scattering on said protein molecule.

27. The method of claim 19, wherein said atomic displacement component of each atom in said one of said plurality of protein vibration modes is calculated by performing Quasi-Harmonic Analysis (QHA) calculation on said protein molecule.

28. The method claim 19, further comprising determining a dynamical behavior of a reaction trajectory along a reaction coordinate of said catalytic reaction.

29. The method of claim 18, further comprising:
providing a model for said protein-mediated reaction including a description of said reaction coordinate; and
generating samples of conformations of said protein molecule along said reaction coordinate, wherein said plurality of protein vibration modes are selected among protein vibration modes that are prevalent during said catalytic reaction from said samples of conformations of said protein molecule.

30. The method of claim 18, further comprising identifying protein regions that show a large conformational fluctuation in said protein molecule in said selected protein vibration mode, wherein said dynamically active residue is located in said identified protein regions.

31. The method of claim 18, further comprising:
selecting at least another protein vibration mode from said plurality of protein vibration modes based on said degree of overlap of reaction coordinate distribution in each of said plurality of protein vibration modes with said reaction coordinate range of said catalytic reaction; and
analyzing conformational fluctuation in said protein molecule in said selected protein vibration mode and said selected at least another protein vibration mode, wherein said dynamically active residue is identified by said analyzing of said conformational fluctuation.

32. The method of claim 18, further comprising:
identifying at least another dynamically active residue; and
calculating dynamic cross-correlation factors at a time scale of interaction among said dynamically active residue and said at least another dynamically active residue.

33. The method of claim 32, further comprising:
analyzing said interactions across a multiple species of protein molecules including said protein molecule; and
identifying a protein vibration network of interactions from a surface of said protein molecule to an active site of said protein molecule by which energy is transferred to said catalytic reaction.

34. The method of claim 14, wherein said protein molecule is one of a dinucleotide binding Rossmann fold protein molecule and a cyclophilin A molecule.

35. The method of claim 14, wherein said magnitude of atomic displacement of atoms is increased by at least one of mechanical means, an elevated temperature, light illumination, a change in pH of a solution, supplementary source of chemical energy and radioactivity.

36. The method of claim 14, wherein said activator is covalently attached to said dynamically active residue.

37. The method of claim 14, wherein said activator attached to said dynamically active residue is located outside an active site of said protein molecule.

38. The method of claim 14, wherein an increase in said magnitude of atomic displacement of atoms in said selected protein vibration mode enhances said chemical reaction rate of said protein-mediated reaction.

39. The method of claim 14, wherein said dynamically active residue is identified by determining a degree of overlap of a reaction coordinate distribution of said protein vibration mode with said reaction pathway range of said catalytic reaction.

* * * * *